United States Patent
Matsumura et al.

(10) Patent No.: US 11,311,626 B2
(45) Date of Patent: Apr. 26, 2022

(54) PLASMIN-CLEAVABLE ANTI-INSOLUBLE FIBRIN ANTIBODY-DRUG CONJUGATE

(71) Applicants: NATIONAL CANCER CENTER JAPAN, Tokyo (JP); RIN INSTITUTE INC., Tokyo (JP)

(72) Inventors: Yasuhiro Matsumura, Chiba (JP); Shino Manabe, Chiba (JP); Hirobumi Fuchigami, Chiba (JP)

(73) Assignees: NATIONAL CANCER CENTER JAPAN, Tokyo (JP); RIN INSTITUTE INC., Tokyo (JP)

( * ) Notice: Subject to any disclaimer, the term of this patent is extended or adjusted under 35 U.S.C. 154(b) by 110 days.

(21) Appl. No.: 16/609,668

(22) PCT Filed: Apr. 27, 2018

(86) PCT No.: PCT/JP2018/017123
§ 371 (c)(1),
(2) Date: Oct. 30, 2019

(87) PCT Pub. No.: WO2018/203517
PCT Pub. Date: Nov. 8, 2018

(65) Prior Publication Data
US 2020/0147231 A1 May 14, 2020

(30) Foreign Application Priority Data
May 2, 2017 (JP) .............................. JP2017-091639

(51) Int. Cl.
*C07K 16/36* (2006.01)
*A61K 47/68* (2017.01)

(52) U.S. Cl.
CPC .......... *A61K 47/6803* (2017.08); *C07K 16/36* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 9,429,584 | B2 * | 8/2016 | Matsumura | ............. | C07K 16/18 |
| 2011/0287036 | A1 * | 11/2011 | Matsumura | ......... | A61K 47/6843 424/181.1 |
| 2016/0011217 | A1 * | 1/2016 | Matsumura | ......... | A61K 47/6843 435/7.92 |

FOREIGN PATENT DOCUMENTS

| EP | 2359852 A1 | 8/2011 |
| WO | WO-89/12690 A1 | 12/1989 |
| WO | WO-00/64946 A2 | 11/2000 |
| WO | WO-03/00736 A1 | 1/2003 |
| WO | WO-2010/055950 A1 | 5/2010 |
| WO | WO-2011/158973 A1 | 12/2011 |
| WO | WO-2014/133093 A1 | 9/2014 |
| WO | WO-2016/167227 A1 | 10/2016 |

OTHER PUBLICATIONS

Manabe et al., Med. Chem. Commun, 2013,4, 792-796, https://doi.org/10.1039/C3MD00075C.*
Manabe et al., Med. Chem. Commun., 2013, 4, 792. DOI https://doi.org/10.1039/C3MD00075C.*
Edwards et al., J Mol Biol. Nov. 14, 2003;334(1):103-18.*
Lloyd et al., Protein Eng Des Sel. Mar. 2009;22(3):159-68. doi: 10.1093/protein/gzn058. Epub Oct. 29, 2008.*
Goel et al., J Immunol. Dec. 15, 2004;173(12):7358-67.*
Kanyavuz et al., Nat Rev Immunol. Jun. 2019;19(6):355-368. doi: 10.1038/S41577-019-0126-7.*
Janeway et al., Immunobiology, 3rd edition, 1997 Garland Publishing Inc., p. 3:1-3:11.*
Rudikoff et al., Proc Natl Acad Sci USA. Mar. 1982;79(6):1979-83.*
Extended European Search Report dated Dec. 8, 2020, for European Patent Application No. 18794602.5, Matsumura et al., "Plasmin-Cleavable Anti-Insoluble Fibrin Antibody-Drug Conjugate," filed Apr. 27, 2018 (9 pages).
Blom et al., "Malignancies, prothrombotic mutations, and the risk of venous thrombosis," JAMA. 293(6):715-22 (2005).
Cavallaro et al., "Polymeric prodrug for release of an antitumoral agent by specific enzymes," Bioconjug Chem. 12(2):143-51 (2001).
De Groot et al., "Design, synthesis, and biological evaluation of a dual tumor-specific motive containing integrin-targeted plasmin-cleavable doxorubicin prodrug," Mol Cancer Ther. 1(11):901-11 (2002).
International Search Report dated Jul. 24, 2018 for PCT International Application No. PCT/JP2018/017123, Matsumura et al., "Plasmin-cleavable Anti-insoluble Fibrin Antibody-drug Conjugate," filed Apr. 27, 2018 (4 pages).
Allgayer et al., "Tumor-associated proteases and inhibitors in gastric cancer: analysis of prognostic impact and individual risk protease patterns," Clin. Exp. Metastasis 16(1):62-73 (1998).

* cited by examiner

*Primary Examiner* — Michael Szperka
(74) *Attorney, Agent, or Firm* — Clark & Elbing LLP; Susan M. Michaud

(57) ABSTRACT

The present invention relates to an antibody-drug conjugate (ADC) and a composition containing the conjugate for use in treating cancer. According to the present invention, provided are an ADC of an antibody specific to insoluble fibrin and a drug in which a linker linking the antibody and the drug has a plasmin cleavage sequence, and a pharmaceutical composition containing the ADC for use in treating cancer.

11 Claims, 7 Drawing Sheets
Specification includes a Sequence Listing.

ANTITUMOR EFFECT

SEQUENCE LISTING

```
<160> NUMBER OF SEQ ID NOS: 28

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Gly Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Trp Ile Asn Thr Lys Ile Gly Glu Pro Thr Tyr Ala Glu Glu Phe Lys
```

```
1               5                   10                  15
Gly

<210> SEQ ID NO 3
<211> LENGTH: 4
<212> TYPE: PRT
<213> ORGANISM: Artificial Sequence
<220> FEATURE:
<223> OTHER INFORMATION: Synthetic Construct

<400> SEQUENCE: 3

Leu Leu Asp Tyr
1

<210> SEQ ID NO 4
<211> LENGTH: 140
<212> TYPE: PRT
<213> ORGANISM: Artificial Sequence
<220> FEATURE:
<223> OTHER INFORMATION: Synthetic Construct

<400> SEQUENCE: 4

Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Lys Ile Gly Glu Pro Thr Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Leu Leu Asp Tyr Trp Gly Gln Gly Thr Thr Leu
        115                 120                 125

Thr Val Ser Ser Ala Lys Thr Thr Pro Pro Ser Val
    130                 135                 140

<210> SEQ ID NO 5
<211> LENGTH: 15
<212> TYPE: PRT
<213> ORGANISM: Artificial Sequence
<220> FEATURE:
<223> OTHER INFORMATION: Synthetic Construct

<400> SEQUENCE: 5

Arg Ala Ser Glu Ser Val Asp Ser Tyr Gly Asn Ser Phe Met His
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Arg Ala Ser Asn Leu Glu Ser
1               5
```

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Ser Asn Glu Asp Pro Arg Thr
1               5

<210> SEQ ID NO 8
<211> LENGTH: 140
<212> TYPE: PRT
<213> ORGANISM: Artificial Sequence
<220> FEATURE:
<223> OTHER INFORMATION: Synthetic Construct

<400> SEQUENCE: 8

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Arg Ala Ser Asn Leu Glu Ser
65                  70                  75                  80

Gly Ile Pro Ala Arg Phe Ser Gly Ser Gly Ser Arg Thr Asp Phe Thr
                85                  90                  95

Leu Thr Ile Asn Pro Val Glu Ala Asp Asp Val Ala Thr Tyr Tyr Cys
            100                 105                 110

Gln Gln Ser Asn Glu Asp Pro Arg Thr Phe Gly Gly Gly Thr Lys Leu
        115                 120                 125

Glu Ile Lys Arg Ala Asp Ala Ala Pro Thr Val Ser
    130                 135                 140

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Ser Tyr Trp Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Ala Ile Tyr Pro Gly Asn Ser Asp Thr Arg Asn Asn Gln Lys Phe Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Lys Ala His Tyr Gly Asn Tyr Gly Phe Ala Tyr
1               5                   10

<210> SEQ ID NO 12
<211> LENGTH: 140
<212> TYPE: PRT
<213> ORGANISM: Artificial Sequence
<220> FEATURE:
<223> OTHER INFORMATION: Synthetic Construct

<400> SEQUENCE: 12

Met Glu Cys Asn Trp Ile Leu Pro Phe Ile Leu Ser Val Ile Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Ala Ser Gly Phe Ser Phe
        35                  40                  45

Thr Ser Tyr Trp Met His Trp Val Lys Gln Arg Pro Gly Gln Gly Leu
    50                  55                  60

Glu Trp Ile Gly Ala Ile Tyr Pro Gly Asn Ser Asp Thr Arg Asn Asn
65                  70                  75                  80

Gln Lys Phe Lys Gly Lys Ala Lys Leu Thr Ala Val Thr Ser Ala Asn
                85                  90                  95

Thr Ala Tyr Met Glu Leu Ser Ser Leu Thr Asn Glu Asp Ser Ala Val
            100                 105                 110

Tyr Tyr Cys Thr Arg Lys Ala His Tyr Gly Asn Tyr Gly Phe Ala Tyr
        115                 120                 125

Trp Gly Gln Gly Thr Leu Val Thr Val Ser Ala Ala
    130                 135                 140

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Lys Ala Ser Asp His Ile Asn Asn Trp Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Gly Ala Thr Ser Leu Glu Thr
1               5

<210> SEQ ID NO 15
<211> LENGTH: 9

```
<212> TYPE: PRT
<213> ORGANISM: Artificial Sequence
<220> FEATURE:
<223> OTHER INFORMATION: Synthetic Construct

<400> SEQUENCE: 15

Gln Gln Tyr Trp Ser Thr Pro Leu Thr
1               5

<210> SEQ ID NO 16
<211> LENGTH: 140
<212> TYPE: PRT
<213> ORGANISM: Artificial Sequence
<220> FEATURE:
<223> OTHER INFORMATION: Synthetic Construct

<400> SEQUENCE: 16

Met Ser Gly His Ser Arg Asn Met Lys Phe Pro Ser Gln Leu Leu Leu
1               5                   10                  15

Phe Leu Leu Phe Arg Ile Thr Gly Ile Ile Cys Asp Ile Gln Met Thr
            20                  25                  30

Gln Ser Ser Ser Tyr Leu Ser Val Ser Leu Gly Gly Arg Val Thr Ile
        35                  40                  45

Thr Cys Lys Ala Ser Asp His Ile Asn Asn Trp Leu Ala Trp Tyr Gln
    50                  55                  60

Gln Lys Pro Gly Asn Ala Pro Arg Leu Leu Ile Ser Gly Ala Thr Ser
65                  70                  75                  80

Leu Glu Thr Gly Val Pro Ser Arg Phe Ser Gly Ser Gly Ser Gly Lys
                85                  90                  95

Asp Tyr Thr Leu Ser Ile Thr Ser Leu Gln Thr Glu Asp Val Ala Thr
            100                 105                 110

Tyr Tyr Cys Gln Gln Tyr Trp Ser Thr Pro Leu Thr Phe Gly Ala Gly
        115                 120                 125

Thr Lys Leu Glu Leu Lys Arg Ala Asp Ala Ala Pro
    130                 135                 140

<210> SEQ ID NO 17
<211> LENGTH: 5
<212> TYPE: PRT
<213> ORGANISM: Artificial Sequence
<220> FEATURE:
<223> OTHER INFORMATION: Synthetic Construct

<400> SEQUENCE: 17

Ser Tyr Ala Met Ser
1               5

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Ala Ile Ser Ser Gly Gly Thr Thr Tyr Tyr Pro Asp Ser Val Lys Gly
1               5                   10                  15

<210> SEQ ID NO 19
<211> LENGTH: 8
<212> TYPE: PRT
<213> ORGANISM: Artificial Sequence
<220> FEATURE:
```

-continued

```
<223> OTHER INFORMATION: Synthetic Construct

<400> SEQUENCE: 19

Gly Gly Thr Ile Gly Ala Tyr Trp
1               5

<210> SEQ ID NO 20
<211> LENGTH: 134
<212> TYPE: PRT
<213> ORGANISM: Artificial Sequence
<220> FEATURE:
<223> OTHER INFORMATION: Synthetic Construct

<400> SEQUENCE: 20

Met Asn Phe Gly Phe Ser Leu Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Ala Ile Ser Ser Gly Gly Thr Thr Tyr Tyr Pro Asp
65                  70                  75                  80

Ser Val Lys Gly Arg Phe Thr Ile Ser Arg Asp Asn Ala Arg Asn Ile
                85                  90                  95

Leu Tyr Leu Gln Met Ser Ser Leu Arg Ser Glu Asp Thr Ala Met Tyr
            100                 105                 110

Tyr Cys Val Arg Gly Gly Thr Ile Gly Ala Tyr Trp Gly Gln Gly Thr
        115                 120                 125

Leu Val Thr Val Ser Ala
    130

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Lys Ser Ser Gln Ser Val Leu Tyr Ser Ser Asn Gln Lys Asn Tyr Leu
1               5                   10                  15

Ala

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Trp Ala Ser Thr Arg Glu Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Construct
```

<400> SEQUENCE: 23

His Gln Tyr Leu Ser Ser Trp Thr
1               5

<210> SEQ ID NO 24
<211> LENGTH: 132
<212> TYPE: PRT
<213> ORGANISM: Artificial Sequence
<220> FEATURE:
<223> OTHER INFORMATION: Synthetic Construct

<400> SEQUENCE: 24

Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Ser Leu Ala
            20                  25                  30

Val Ser Ala Gly Glu Lys Val Thr Met Ser Cys Lys Ser Ser Gln Ser
        35                  40                  45

Val Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Leu Ser Ser Trp Thr Phe Gly Gly Gly Thr Lys
        115                 120                 125

Leu Glu Ile Lys
    130

<210> SEQ ID NO 25
<211> LENGTH: 491
<212> TYPE: PRT
<213> ORGANISM: Homo sapiens

<400> SEQUENCE: 25

Met Lys Arg Met Val Ser Trp Ser Phe His Lys Leu Lys Thr Met Lys
1               5                   10                  15

His Leu Leu Leu Leu Leu Leu Cys Val Phe Leu Val Lys Ser Gln Gly
            20                  25                  30

Val Asn Asp Asn Glu Glu Gly Phe Phe Ser Ala Arg Gly His Arg Pro
        35                  40                  45

Leu Asp Lys Lys Arg Glu Glu Ala Pro Ser Leu Arg Pro Ala Pro Pro
    50                  55                  60

Pro Ile Ser Gly Gly Gly Tyr Arg Ala Arg Pro Ala Lys Ala Ala Ala
65                  70                  75                  80

Thr Gln Lys Lys Val Glu Arg Lys Ala Pro Asp Ala Gly Gly Cys Leu
                85                  90                  95

His Ala Asp Pro Asp Leu Gly Val Leu Cys Pro Thr Gly Cys Gln Leu
            100                 105                 110

Gln Glu Ala Leu Leu Gln Gln Glu Arg Pro Ile Arg Asn Ser Val Asp
        115                 120                 125

Glu Leu Asn Asn Asn Val Glu Ala Val Ser Gln Thr Ser Ser Ser Ser
    130                 135                 140

Phe Gln Tyr Met Tyr Leu Leu Lys Asp Leu Trp Gln Lys Arg Gln Lys

```
            145                 150                 155                 160
        Gln Val Lys Asp Asn Glu Asn Val Val Asn Glu Tyr Ser Ser Glu Leu
                        165                 170                 175
        Glu Lys His Gln Leu Tyr Ile Asp Glu Thr Val Asn Ser Asn Ile Pro
                        180                 185                 190
        Thr Asn Leu Arg Val Leu Arg Ser Ile Leu Glu Asn Leu Arg Ser Lys
                        195                 200                 205
        Ile Gln Lys Leu Glu Ser Asp Val Ser Ala Gln Met Glu Tyr Cys Arg
                    210                 215                 220
        Thr Pro Cys Thr Val Ser Cys Asn Ile Pro Val Val Ser Gly Lys Glu
        225                 230                 235                 240
        Cys Glu Glu Ile Ile Arg Lys Gly Gly Glu Thr Ser Glu Met Tyr Leu
                                245                 250                 255
        Ile Gln Pro Asp Ser Ser Val Lys Pro Tyr Arg Val Tyr Cys Asp Met
                        260                 265                 270
        Asn Thr Glu Asn Gly Gly Trp Thr Val Ile Gln Asn Arg Gln Asp Gly
                    275                 280                 285
        Ser Val Asp Phe Gly Arg Lys Trp Asp Pro Tyr Lys Gln Gly Phe Gly
                    290                 295                 300
        Asn Val Ala Thr Asn Thr Asp Gly Lys Asn Tyr Cys Gly Leu Pro Gly
        305                 310                 315                 320
        Glu Tyr Trp Leu Gly Asn Asp Lys Ile Ser Gln Leu Thr Arg Met Gly
                                325                 330                 335
        Pro Thr Glu Leu Leu Ile Glu Met Glu Asp Trp Lys Gly Asp Lys Val
                        340                 345                 350
        Lys Ala His Tyr Gly Gly Phe Thr Val Gln Asn Glu Ala Asn Lys Tyr
                    355                 360                 365
        Gln Ile Ser Val Asn Lys Tyr Arg Gly Thr Ala Gly Asn Ala Leu Met
                    370                 375                 380
        Asp Gly Ala Ser Gln Leu Met Gly Glu Asn Arg Thr Met Thr Ile His
        385                 390                 395                 400
        Asn Gly Met Phe Phe Ser Thr Tyr Asp Arg Asp Asn Asp Gly Trp Leu
                                405                 410                 415
        Thr Ser Asp Pro Arg Lys Gln Cys Ser Lys Glu Asp Gly Gly Gly Trp
                        420                 425                 430
        Trp Tyr Asn Arg Cys His Ala Ala Asn Pro Asn Gly Arg Tyr Tyr Trp
                    435                 440                 445
        Gly Gly Gln Tyr Thr Trp Asp Met Ala Lys His Gly Thr Asp Asp Gly
                450                 455                 460
        Val Val Trp Met Asn Trp Lys Gly Ser Trp Tyr Ser Met Arg Lys Met
        465                 470                 475                 480
        Ser Met Lys Ile Arg Pro Phe Phe Pro Gln Gln
                        485                 490

<210> SEQ ID NO 26
<211> LENGTH: 102
<212> TYPE: PRT
<213> ORGANISM: Artificial Sequence
<220> FEATURE:
<223> OTHER INFORMATION: Synthetic Construct

<400> SEQUENCE: 26

Met Glu Asp Ser Thr Thr Asn Ile Thr Lys His Gln Lys Trp Thr Val
1               5                   10                  15

Glu Glu Ser Glu Trp Val Lys Ala Gly Val Gln Lys Tyr Gly Glu Gly
```

```
                    20                  25                  30

Asn Trp Ala Ala Ile Ser Lys Asn Tyr Pro Phe Val Asn Arg Thr Ala
                35                  40                  45

His Met Ile Lys His Arg Trp Arg His Met Lys Arg Leu Gly Met Asn
            50                  55                  60

Ser Gly Thr Asn Leu Val Pro Arg Gly Ser Gly Ile Glu Gly Arg Thr
65                  70                  75                  80

Met Ala Ile Ser Asp Pro Asn Ser Ser Cys Asn Ile Pro Val Val
                85                  90                  95

Ser Gly Lys Glu Cys Glu
            100
```

<210> SEQ ID NO 27
<211> LENGTH: 265
<212> TYPE: PRT
<213> ORGANISM: Artificial Sequence
<220> FEATURE:
<223> OTHER INFORMATION: Synthetic Construct

<400> SEQUENCE: 27

```
Met Thr Val Ser Cys Asn Ile Pro Val Val Ser Gly Lys Glu Cys Glu
1               5                   10                  15

Glu Ile Ile Arg Lys Gly Gly Glu Thr Ser Glu Met Tyr Leu Ile Gln
                20                  25                  30

Pro Asp Ser Ser Val Lys Pro Tyr Arg Val Tyr Cys Asp Met Asn Thr
            35                  40                  45

Glu Asn Gly Gly Trp Thr Val Ile Gln Asn Arg Gln Asp Gly Ser Val
        50                  55                  60

Asp Phe Gly Arg Lys Trp Asp Pro Tyr Lys Gln Gly Phe Gly Asn Val
65                  70                  75                  80

Ala Thr Asn Thr Asp Gly Lys Asn Tyr Cys Gly Leu Pro Gly Glu Tyr
                85                  90                  95

Trp Leu Gly Asn Asp Lys Ile Ser Gln Leu Thr Arg Met Gly Pro Thr
            100                 105                 110

Glu Leu Leu Ile Glu Met Glu Asp Trp Lys Gly Asp Lys Val Lys Ala
        115                 120                 125

His Tyr Gly Gly Phe Thr Val Gln Asn Glu Ala Asn Lys Tyr Gln Ile
130                 135                 140

Ser Val Asn Lys Tyr Arg Gly Thr Ala Gly Asn Ala Leu Met Asp Gly
145                 150                 155                 160

Ala Ser Gln Leu Met Gly Glu Asn Arg Thr Met Thr Ile His Asn Gly
                165                 170                 175

Met Phe Phe Ser Thr Tyr Asp Arg Asp Asn Asp Gly Trp Leu Thr Ser
            180                 185                 190

Asp Pro Arg Lys Gln Cys Ser Lys Glu Asp Gly Gly Trp Trp Tyr
        195                 200                 205

Asn Arg Cys His Ala Ala Asn Pro Asn Gly Arg Tyr Tyr Trp Gly Gly
        210                 215                 220

Gln Tyr Thr Trp Asp Met Ala Lys His Gly Thr Asp Asp Gly Val Val
225                 230                 235                 240

Trp Met Asn Trp Lys Gly Ser Trp Tyr Ser Met Arg Lys Met Ser Met
                245                 250                 255

Lys Ile Arg Pro Phe Phe Pro Gln Gln
            260                 265
```

```
<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Cys Asn Ile Pro Val Val Ser Gly Lys Glu Cys Glu
1               5                   10
```

PLASMIN-CLEAVABLE ANTI-INSOLUBLE FIBRIN ANTIBODY-DRUG CONJUGATE

SEQUENCE LISTING

The instant application contains a Sequence Listing which has been submitted electronically in ASCII format and is hereby incorporated by reference in its entirety. Said ASCII copy, created on Oct. 21, 2019 is named 51021-016001_Sequence_Listing_102119_ST25 and is 20,480 bytes in size.

TECHNICAL FIELD

The present invention relates to an antibody-drug conjugate and a composition containing the conjugate for use in treating cancer.

BACKGROUND ART

It has been revealed that when a blood vessel is injured, if blood comes into contact with the damaged blood vessel wall or the blood vessel subendothelial tissue or a tissue factor flows into the bloodstream, a blood coagulation reaction starts, the fibrinogen in blood or pathological lesion changes into insoluble fibrin, and a net of fibrin functions as a strong hemostatic plug to harden the wound.

It has long been suggested that blood coagulation is closely related to cancer (described in the "Plegmasia alba dolens"—by a French physician in 1800s, Trousseau) Recent clinical epidemiological data have also revealed that most cancers, including pancreatic cancer, gastric cancer, and brain tumor, have a significantly higher frequency of thrombosis due to hypercoagulation than healthy individuals (Non-Patent Literature 1). In addition, it is considered that accumulation of insoluble fibrin, coagulative necrosis, and angiogenesis due to abnormal coagulation occur repeatedly also inside cancer tissues with the progress of the cancer.

Insoluble fibrin is not present in tissues under normal physiological conditions, unlike fibrinogen, which is a precursor of fibrin, being widely present in the living body. Fibrinogen is cleaved by activated thrombin leaked to the outside of a blood vessel to form a fibrin monomer, and the fibrin monomer polymerizes and crosslinks to form fibrin fibers. Thus, insoluble fibrin is generated. Therefore, insoluble fibrin is specifically present in tissues in pathological conditions, such as bleeding and inflammation, and is formed when a pathologic state involving coagulation, such as cancer, myocardial infarction, or cerebral infarction, has occurred. Accordingly, insoluble fibrin is a marker molecule for such thrombus-related diseases. In particular, insoluble fibrin that is present in cancerous tissues not involving cerebral circulatory diseases such as myocardial infarction and cerebral infarction is exactly a cancer-specific molecule.

Under such technical background, an antibody specific to insoluble fibrin and an antibody-drug conjugate (ADC) using the antibody have been proposed (Patent Literature 1).

CITATION LIST

Patent Literature

[Patent Literature 1]
 WO 2014/133093

SUMMARY OF INVENTION

The present inventors have developed an ADC of an antibody specific to insoluble fibrin and a drug, in which a linker linking the antibody and the drug has a plasmin cleavage sequence. The present inventors have found that the resulting ADC is delivered to insoluble fibrin and is cleaved by plasmin at the delivered site to release the drug at the site. Furthermore, the present inventors have found, using a tumor animal model, that the resulting ADC can target an insoluble fibrin accumulation site in the vicinity of a tumor and releases the drug at the site to show an anticancer activity against the tumor. In addition, the present inventors have acquired a new insoluble fibrin-specific antibody. The present invention is based on these findings.

That is, the present invention provides the followings:
(1) An antibody-drug conjugate (ADC), wherein
 the antibody is an antibody that binds to fibrin and has affinity to insoluble fibrin higher than that to fibrinogen,
 the drug is a cytotoxic agent, and
 the antibody and the drug are linked to each other through a linker having a plasmin cleavage site that allows cleavage by plasmin;
(2) The ADC according to (1), wherein
 the linker comprises a valine-leucine-lysine peptide sequence as the plasmin cleavage site;
(3) A pharmaceutical composition comprising the ADC according to (1) or (2) for use in treating cancer;
(4) The pharmaceutical composition according to (3), wherein the cancer is invasive cancer;
(5) An antibody that binds to fibrin, wherein the antibody has
 a heavy chain variable region having CDR1 set forth in SEQ ID NO: 1, CDR2 set forth in SEQ ID NO: 2, and CDR3 set forth in SEQ ID NO: 3, and
 a light chain variable region having CDR1 set forth in SEQ ID NO: 5, CDR2 set forth in SEQ ID NO: 6, and CDR3 set forth in SEQ ID NO: 7; an antibody that competes with the antibody for binding to fibrin; or an antigen-binding fragment thereof;
(6) An antibody that binds to fibrin, wherein the antibody has
 a heavy chain variable region set forth in SEQ ID NO: 4 and a light chain variable region set forth in SEQ ID NO: 8; or
 an antigen-binding fragment thereof;
(7) An antibody that binds to fibrin, wherein the antibody has
 a heavy chain variable region having CDR1 set forth in SEQ ID NO: 9, CDR2 set forth in SEQ ID NO: 10, and CDR3 set forth in SEQ ID NO: 11, and
 a light chain variable region having CDR1 set forth in SEQ ID NO: 13, CDR2 set forth in SEQ ID NO: 14, and CDR3 set forth in SEQ ID NO: 15;
 an antibody that competes with the antibody for binding to fibrin; or an antigen-binding fragment thereof;
(8) An antibody that binds to fibrin, wherein the antibody has
 a heavy chain variable region set forth in SEQ ID NO: 12 and a light chain variable region set forth in SEQ ID NO: 16; or
 an antigen-binding fragment thereof;
(9) The ADC according to (1) or (2), wherein the antibody is the antibody according to any one of (5) to (8);
(10) A pharmaceutical composition comprising the ADC according to (9); and
(11) The pharmaceutical composition according to (10), for use in treating cancer.

DESCRIPTION OF EMBODIMENTS

Figure 1:
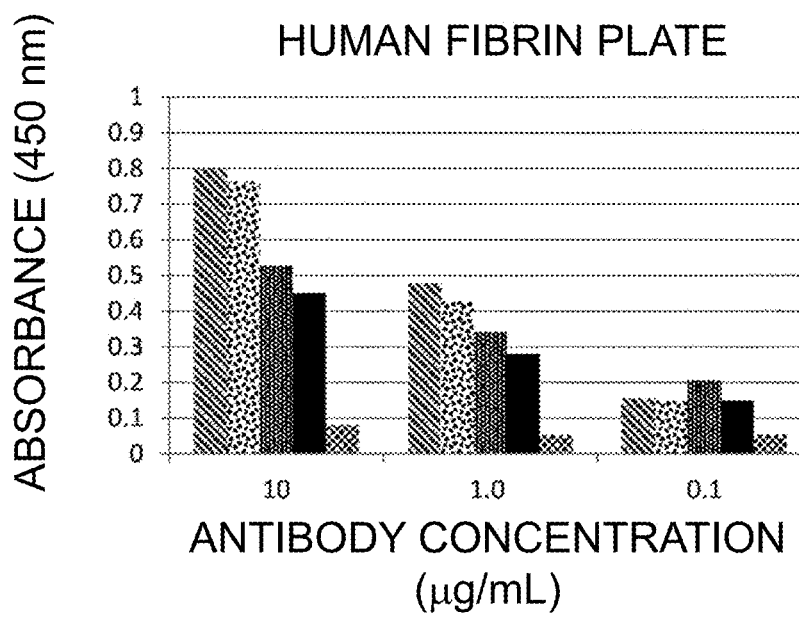
FIG. 1 shows that antibodies obtained by the present invention are specific to insoluble fibrin.
Figure 1:
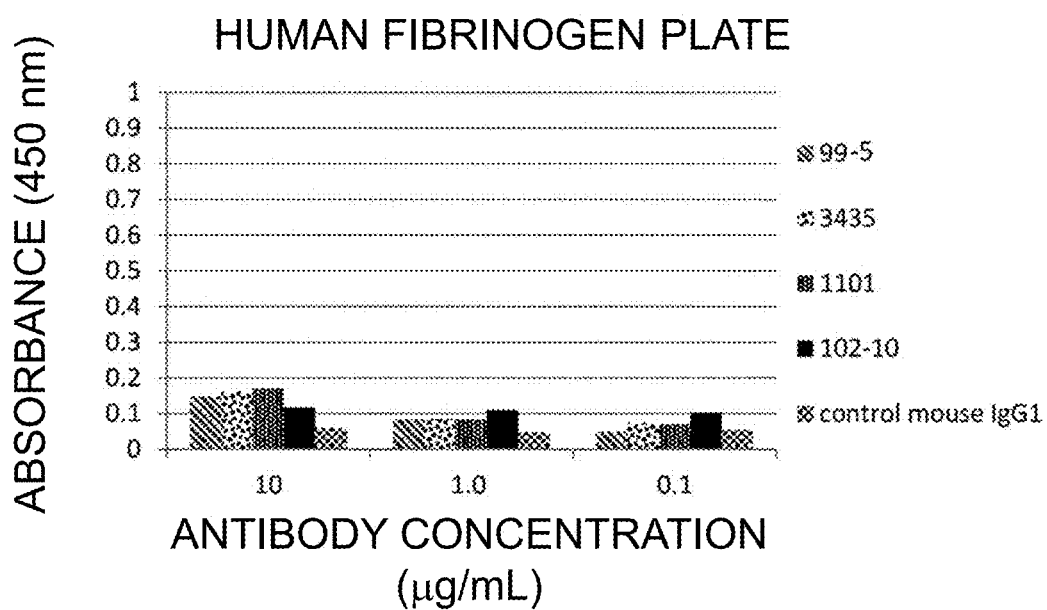

In the present invention, the term "subject" means a mammal, in particular a human.

In the present specification, the term "treatment" is used to mean therapy (therapeutic treatment) and prevention (preventive treatment). In the present specification, the term "therapy" means therapy, cure, or prevention of a disease or a disorder; improvement of remission; or a reduction in the speed of progress of a disease or a disorder. In the present specification, the term "prevention" means a reduction in risk of onset of a disease or a pathologic state or a delay of onset of a disease or a pathologic state.

In the present specification, the term "disease" means a symptom of which therapy is helpful. In the present specification, the term "cancer" means a malignant tumor.

In the present specification, the term "antibody" means an immunoglobulin and encompasses a polyclonal antibody and a monoclonal antibody. A preferred antibody is a monoclonal antibody. Although the origin of the antibody is not particularly limited, examples of the antibody include non-human animal antibodies, non-human mammal antibodies, and human antibodies. The antibody may be a chimera antibody, a humanized antibody, or a human antibody. In addition, the antibody may a bispecific antibody.

In the present specification, the term "therapeutically effective amount" means an amount of a medicine effective for treating (prevention and therapy) of a disease or a condition. A therapeutically effective amount of a medicine can reduce the speed of worsening of a symptom of a disease or a condition, stop the worsening of the symptom, improve the symptom, cure the symptom, or suppress the onset or development of the symptom.

In the present specification, the term "insoluble fibrin" means fibrin crosslinked by factor XIII. In a living body, for example, if bleeding occurs, fibrinogen is converted into a fibrin monomer by the action of thrombin, the fibrinogen monomer polymerizes to form an insoluble fibrin polymer. The fibrin polymer is crosslinked by factor XIII into insoluble fibrin.

In the present specification, the term "insoluble fibrin-specific antibody" is an antibody that binds to insoluble fibrin and has a higher affinity to insoluble fibrin than to fibrinogen. Such an insoluble fibrin-specific antibody can be easily obtained by screening with an affinity to insoluble fibrin and an affinity to fibrinogen. Fibrin has an epitope site that is exposed only when fibrin becomes insoluble by three-dimensional structural change into the insoluble fibrin. Accordingly, the "insoluble fibrin-specific antibody" can be obtained by immunization with the exposed domain, that is, D-domain as an immunogen. Alternatively, the antibody can also be obtained using a linear peptide. For example, an "insoluble fibrin-specific antibody" can be obtained by immunization with a fibrin Bβ chain partial peptide corresponding to positions 231 to 246 of the amino acid sequence of the fibrin Bβ chain (for example, human fibrin Bβ chain can have the amino acid sequence set forth in SEQ ID NO: 25). Alternatively, the "insoluble fibrin-specific antibody" can also be obtained by immunization using a peptide set forth in SEQ ID NO: 26 or SEQ ID NO: 27 as an immunogen. Such an insoluble fibrin-specific antibody can be an antibody having a higher affinity to insoluble fibrin than to all of fibrinogen, fibrin monomers, and fibrin polymers. An antibody having a ratio of the affinity to insoluble fibrin to the affinity to fibrinogen of, for example, higher than 1, 1.5 or more, 2 or more, 3 or more, 4 or more, or 5 or more can be obtained as an insoluble fibrin-specific antibody. The affinity means binding affinity (KD) and can be determined by a known method, such as ELISA and kinetic exclusion assay.

In the present specification, the term "compete" means scrambling with another binding antibody for binding to an antigen. Competition can occur when two antibodies have binding sites for the same antigen. Such antibodies can be obtained by immunization using an epitope described above and/or also by verifying by competitive assay whether binding of one antibody to an antigen is reduced by the other antibody or not.

In the present specification, the term "antibody-drug conjugate" (hereinafter, also referred to as "ADC") means a substance in which an antibody and a cytotoxic agent are linked to each other. In the ADC, the antibody and the cytotoxic agent can be linked to each other via an appropriate linker. As the cytotoxic agent, a chemotherapeutic agent, a radioisotope, or a toxin can be used. The term "ADC" encompasses a conjugate of an antigen-binding fragment of an antibody and a drug.

In the present specification, the term "antigen-binding fragment" means a part of an antibody in which the affinity to an antigen is maintained. The antigen-binding fragment can comprise the heavy chain variable region, the light chain variable region, or the both in the antibody of the present invention. The antigen-binding fragment may be chimerized or humanized. Examples of the antigen-binding fragment include Fab, Fab', F(ab')$_2$, Fv, scFv (single-chain Fv), diabody, and sc(Fv)$_2$ (single-chain (Fv)$_2$). Such antibody fragments can be obtained by, but not particularly limited to, treating the antibody with an enzyme. For example, digestion of an antibody with papain gives Fab. Alternatively, digestion of an antibody with pepsin gives F(ab')$_2$, and Fab' can be obtained by further reduction of the F(ab')$_2$. In the present invention, such antigen-binding fragments of an antibody can be used.

In the present invention, the antibody and the cytotoxic agent in an antibody-drug conjugate are linked to each other via a linker. Examples of the cytotoxic agent include chemotherapeutic agents (for example, anticancer agents such as commercially available anticancer agents, e.g., auristatin (auristatin E, auristatin F phenylenediamine (AFP), monomethyl auristatin E, monomethyl auristatin F, and derivatives thereof), maytansinoids DM1 and DM4, and derivatives thereof), camptothecin (SN-38, irinotecan, Lurtotecan, DB67, BMP1350, ST1481, CKD602, topotecan, and exatecan, and derivatives thereof), DNA minor groove binding agents (enediyne, lexitropsin, and duocarmycin, and derivatives thereof), taxanes (paclitaxel and docetaxel, and derivatives thereof), polyketides (discodermolide and derivatives thereof), anthraquinones (mitoxantrone and derivatives thereof), benzodiazepine (pyrrolobenzodiazepine, indolinobenzodiazepine, and oxazolidinobenzodiazepine, and derivatives thereof), vinca alkaloids (vincristine, vinblastine, vindesine, and vinorelbine, and derivatives thereof), doxorubicins (doxorubicin, morpholino-doxorubicin, and cyanomorpholino-doxorubicin, and derivatives thereof), cardiac glycosides (digitoxin and derivatives thereof), calicheamicin, epothilone, cryptophycin, cemadotin, cemadotin, rhizoxin, netropsin, combrestatin, eluterobin, etoposide, T67 (tularik), and nocodazole); radioisotopes (for example, $^{32}P$, $^{60}C$, $^{90}Y$, $^{111}In$, $^{131}I$, $^{125}I$, $^{153}Sm$, $^{186}Re$, $^{188}Re$, and $^{212}Bi$); and toxins (for example, diphtheria toxin A, Pseudomonas endotoxin, ricin, and saporin), and they can be used as the cytotoxic agent in the ADC of the present invention. As the cytotoxic agent in the ADC of the present invention, preferably, for example, camptothecin, in particular SN-38 or exatecan can be used. As the cytotoxic agent, any of those used for treatment of cancer can be used. The cytotoxic agent may be a pharmaceutically acceptable salt, a solvate (for example, hydrate), an ester, or a prodrug of the above-mentioned cytotoxic agents.

In the present invention, the linker of the ADC comprises a plasmin cleavage sequence and can be cleaved in the presence of plasmin. In the present invention, the linker of the ADC, the parts other than the plasmin cleavage sequence comprise chemical bonds that are stable in the process from administration to delivery to insoluble fibrin. The ADC of the present invention in such a constitution is stable after administration until being delivered to insoluble fibrin and is cleaved by plasmin after binding to insoluble fibrin to release the cytotoxic agent in the vicinity of the insoluble fibrin. The plasmin cleavage sequence is an amino acid sequence and, specifically, can be a peptide chain comprising an amino acid sequence such as a plasmin cleavage sequence selected from the group consisting of valine-leucine-lysine, glycine-proline-lysine, glutamic acid-lysine-lysine, lysine-phenylalanine-lysine, norvaline-chlorohexyl-alanyl-lysine, and norleucine-hexahydrotyrosine-lysine. Such a linker can be appropriately selected in production of the ADC and synthesized by a person skilled in the art. In a certain aspect, as the linker, for example, a first space may be inserted between the antibody and the plasmin cleavage sequence, where for example, polyethylene glycol (PEG), such as PEG with about 5 to 40 repeating units per molecule, can be used as the first spacer; and a second spacer may be inserted between the plasmin cleavage sequence and the cytotoxic agent, where for example, p-aminobenzyloxycarbonyl (PABC) can be used as the second spacer.

In a certain aspect, the linker comprises a first spacer and a plasmin cleavage sequence. In a certain aspect, the linker comprises a first spacer, a plasmin cleavage sequence, and a second spacer. In a certain subject, the linker comprises PEG, a plasmin cleavage sequence, and PABC.

In a certain aspect, the linker does not comprise cleavable moieties other than the plasmin cleavage sequence.

In the binding between an antibody and the linker, for example, the linker can be linked to a sulfhydryl group of the antibody via a maleimide group.

In a certain aspect, the antibody is linked to an anticancer agent via its sulfhydryl group through a linker having a maleimide-PEG-plasmin cleavage sequence. In a certain aspect, the antibody is linked to an anticancer agent via its sulfhydryl group through a linker having maleimide-PEG-plasmin cleavage sequence-PABC.

In any case, in the ADC of the present invention, an anticancer agent is linked to an anticancer agent through a linker having a plasmin cleavage site that can be cleaved by plasmin, and when the ADC reached an insoluble fibrin accumulation site, the linker is cleaved at the plasmin cleavage site by plasmin present in the circumference thereof to release the anticancer agent to the vicinity of the insoluble fibrin. It is considered that in the vicinity of cancer tissue, there are many insoluble fibrin accumulation sites due to bleeding caused by cancer invasion (see FIG. 8), and it is considered that the antibody of the present invention (i.e., insoluble fibrin-specific antibody) is useful for targeting to cancer in a drug delivery system, and the ADC of the present invention is useful as a therapeutic agent for cancer.

The present invention provides the following antibodies:
an antibody that binds to fibrin, wherein the antibody has a heavy chain variable region having CDR1 set forth in SEQ ID NO: 1, CDR2 set forth in SEQ ID NO: 2, and CDR3 set forth in SEQ ID NO: 3, and
a light chain variable region having CDR1 set forth in SEQ ID NO: 5, CDR2 set forth in SEQ ID NO: 6, and CDR3 set forth in SEQ ID NO: 7; and
an antibody that competes with the antibody for binding to fibrin. These antibodies can be used as the insoluble fibrin-specific antibody.

The present invention also provides the following antibody:
an antibody that binds to fibrin, wherein the antibody has a heavy chain variable region set forth in SEQ ID NO: 4 and a light chain variable region set forth in SEQ ID NO: 8. This antibody can be used as the insoluble fibrin-specific antibody.

This antibody is also recognized as an antibody having
a heavy chain variable region having CDR1 set forth in SEQ ID NO: 1, CDR2 set forth in SEQ ID NO: 2, and CDR3 set forth in SEQ ID NO: 3, and
a light chain variable region having CDR1 set forth in SEQ ID NO: 5, CDR2 set forth in SEQ ID NO: 6, and CDR3 set forth in SEQ ID NO: 7.

The present invention provides the following antibodies:
an antibody that binds to fibrin, wherein the antibody has a heavy chain variable region having CDR1 set forth in SEQ ID NO: 9, CDR2 set forth in SEQ ID NO: 10, and CDR3 set forth in SEQ ID NO: 11, and
a light chain variable region having CDR1 set forth in SEQ ID NO: 13, CDR2 set forth in SEQ ID NO: 14, and CDR3 set forth in SEQ ID NO: 15; and
an antibody that competes with the antibody for binding to fibrin. These antibodies can be used as the insoluble fibrin-specific antibody.

The present invention also provides the following antibody:
an antibody that binds to fibrin, wherein the antibody has a heavy chain variable region set forth in SEQ ID NO: 12 and a light chain variable region set forth in SEQ ID NO: 16. This antibody can be used as the insoluble fibrin-specific antibody.

This antibody is also recognized as an antibody having
a heavy chain variable region having CDR1 set forth in SEQ ID NO: 9, CDR2 set forth in SEQ ID NO: 10, and CDR3 set forth in SEQ ID NO: 11, and a light chain variable region having CDR1 set forth in SEQ ID NO: 13, CDR2 set forth in SEQ ID NO: 14, and CDR3 set forth in SEQ ID NO: 15.

The above-mentioned antibodies, insoluble fibrin-specific antibodies, and antigen-binding fragments thereof can be used as the antibody part in the ADC of the present invention.

According to the present invention, a pharmaceutical composition comprising a therapeutically effective amount of the ADC (also referred to as "ADC of the present invention") is provided. According to the present invention, the ADC and the pharmaceutical composition of the present invention can each be used for treating cancer.

The cancer as a subject to be treated by the ADC or the pharmaceutical composition of the present invention is not particularly limited, and examples thereof include lung cancer, pancreatic cancer, head and neck cancer, prostatic cancer, bladder cancer, breast cancer, esophageal cancer, stomach cancer, colon cancer, uterine cancer, ovarian cancer, skin cancer, thyroid cancer, thymic cancer, kidney cancer, testicular cancer, penile cancer, liver cancer, biliary tract cancer, brain tumor, bone and soft tissue tumor, retroperitoneal tumor, and angiosarcoma/lymphangiosarcoma, and metastatic cancers thereof.

The subject of the present invention can be a subject who does not suffer from a thrombotic disorder or a disease associated with a thrombotic disorder or a subject who is not diagnosed to have a thrombotic disorder or a disease associated with a thrombotic disorder. Consequently, it can be expected to reduce side effects at tissues other than cancer. Accordingly, whether a subject having cancer suffers from a thrombotic disorder or a disease associated with a thrombotic disorder or not may be determined, and then the ADC of the present invention may be administered to the subject not suffering from a thrombotic disorder or a disease associated with a thrombotic disorder. Whether a subject suffers from a thrombotic disorder or a disease associated with a thrombotic disorder or not can be appropriately determined by a medical doctor.

In a certain aspect of the present invention, the pharmaceutical composition comprises the ADC of the present invention and an excipient. The pharmaceutical composition of the present invention can be administered by a method, such as intravenous administration, subcutaneous administration, intratumoral administration, intraperitoneal administration, intraventricular administration, and intramuscular administration. The dose can be appropriately determined by a medical doctor in consideration with, for example, the age, sex, weight, and severity of a disease of a patient.

The ADC of the present invention not only targets insoluble fibrin that accumulates in stroma of cancer and allows the cytotoxic agent to accumulate at the target site but also has a linker that can be cleaved by plasmin that is activated at the site where insoluble fibrin is present and causes liberation of the cytotoxic agent at the target site. Consequently, it is possible to site-specifically injure the cancer in the vicinity of the liberation site.

According to the present invention, provided is use of the insoluble fibrin-specific antibody in the manufacture of a medicament for use in treating cancer. According to the present invention, provided is use of an ADC of an insoluble fibrin-specific antibody and a cytotoxic agent, wherein the antibody and cytotoxic agent has a plasmin cleavage site that can be cleaved by plasmin in the ADC, in the manufacture of medicament for use in treating cancer.

According to the present invention, provided is a method for treating cancer in a subject in need thereof, comprising administering a therapeutically effective amount of the ADC of the present invention to the subject. According to the present invention, provided is a method for treating cancer in a subject in need thereof, comprising determining whether a subject having cancer suffers from a thrombotic disorder or a disease associated with a thrombotic disorder or not, and then administering a therapeutically effective amount of the ADC of the present invention to the subject not suffering from a thrombotic disorder or a disease associated with a thrombotic disorder.

According to the present invention, provided is use of the ADC of the present invention for use in a method for treating cancer.

EXAMPLES

Example 1: Production of Insoluble Fibrin-Specific Antibody

In this example, an antibody that has a selectively higher affinity to insoluble fibrin than to fibrinogen (hereinafter, referred to as "insoluble fibrin-specific antibody") was produced.

(1) Explanation of Immunogen

In the example, antibodies were obtained by immunizing animals with a peptide having the amino acid sequence of SEQ ID NO: 26 or a peptide having the amino acid sequence of SEQ ID NO: 27 as immunogens.

(2) Immunization Method

Mice were immunized 6 times every 2 weeks as follows.

The immunogens for the first and the fourth immunization were prepared as follows. A peptide having the amino acid sequence of SEQ ID NO: 26 and a peptide having the amino acid sequence of SEQ ID NO: 27 were each used as immunogens. An immunogen adjusted to 0.5 mg/mL with sterilized PBS was put in a 1-mL syringe. Freund's Complete Adjuvant (Difco) in the same amount as that of the immunogen was put in another 1-mL syringe. The syringes were connected with an adaptor, and extrusion was performed until resistance was felt. In the first and fourth immunization, 200 µL of the immunogen were intraperitoneally administered.

The immunogen for second, third, fifth, and sixth immunization was prepared as follows. An immunogen adjusted to 0.5 mg/mL with sterilized PBS was mixed with GERBU ADJUVANT 100 (nacalai tesque) in the same amount of the immunogen in a 1.5-mL tube, and the mixture was put in a 1-mL syringe. In the second, third, fifth, and sixth immunization, 100 µL of the immunogen were intraperitoneally administered. In the final immunization, an immunogen adjusted to 0.1 mg/mL with sterilized PBS was put in a 1-mL syringe, and 100 µL of the immunogen were first intraperitoneally administered, and after 10 minutes, 400 µL of the immunogen were administered from the tail vein.

(3) Measurement of Antibody Titer

One week before the last immunization of each mouse, blood was collected from the tail vein. The blood was centrifuged at 4,000×g for 10 minutes at 4° C., and the supernatant was collected as a sample. The antibody titer was measured by ELISA using samples prepared by two-fold serial dilution from 100-fold to 12800-fold. In advance of the ELISA, an antigen-immobilized plate was prepared. Fibrinogen from human plasma (SIGMA) was dissolved in TBS (pH 8.5) to produce a 20 µg/mL fibrinogen solution. The solution was added to a 96-well immunoplate at 50 µL/well and was left to stand at 4° C. overnight to prepare a fibrinogen plate. Thrombin diluted to 0.05 NIH U/mL with a thrombin diluent [7 mM L-cysteine (FUJIFILM Wako Pure Chemical Corporation), 1 mM $CaCl_2$ (FUJIFILM Wako Pure Chemical Corporation), TBS (pH 8.5)] was added to the fibrinogen plate at 100 µL/well and was incubated at 37° C. for 2 hours to prepare an insoluble fibrin plate. The plate on which each antigen was immobilized was washed with 200 µL of PBS-T (PBS, 0.5% (v/v) Tween 20) three times, and 200 µL of a blocking solution [PBS-T, 1% (w/v) BSA] were added to each well, followed by being left to stand at room temperature for 1 hour for blocking. The serially diluted samples were added to the plate at 50 µL/well and were left to stand at room temperature for 1 hour. The solutions were discarded, and the plate was washed with PBS-T three times. A secondary antibody diluted to 0.3 µg/mL with the blocking solution was added to the plate at 50 µL/well, followed by being left to stand at room temperature for 30 minutes. As the secondary antibody, polyclonal rabbit anti-mouse immunoglobulins/HRP (Dako) and polyclonal rabbit anti-rat immunoglobulins/HRP (Dako) were used properly according to the sample. The solutions were discarded, the plate was washed with PBS-T three times, and a chromogenic substrate solution (1-Step™ Slow TMB-ELISA Substrate Solution, Thermo Fisher Scientific, Inc.) was added to the plate at 100 µL/well, followed by a reaction at room temperature for 10 minutes. The reaction was stopped by adding 30 µL of 2N $H_2SO_4$ to each well. The absorbance at a wavelength of 450 nm was measured with a Spectra Max paradigm (Molecular Devices).

(4) Preparation of Hybridoma

The spleen was surgically removed from each mouse and immersed in an RPMI 1640 medium supplemented with 200 units/mL penicillin, 200 µg/mL streptomycin, and 500 ng/mL amphotericin B. RPMI 1640 was injected into the spleen using a syringe 10-mL (TERUMO Corporation) and an injection needle 22G (TERUMO Corporation), and spleen cells were taken out and were passed through an EASY strainer 70-µm mesh (Greiner Bio-One). The collected cell suspension was centrifuged at 270×g for 5 minutes at room temperature, the supernatant was removed, and the precipitate was suspended in 10 mL of RPMI 1640. After repeating this washing with RPMI 1640 twice, the precipitate was suspended in 5 mL of RPMI 1640, followed by cell fusion as in cell fusion using mouse iliac lymph nodes.

(5) Screening of Hybridoma

Screening by ELISA was started 10 days after the cell fusion. In primary screening, 50 µL of the culture supernatant from each of all wells were dispensed to use as a primary antibody. Plates on which each of the peptides used for immunization was immobilized were prepared. A peptide was diluted to 20 µg/mL with a phosphate buffer and added to a 96-well immunoplate (MAXI BREAKAPART NUNC-IMMUNO MODULE, Nunc) at 50 µL/well, followed by being left to stand at room temperature for 1 hour for immobilization. After the immobilization, ELISA was performed as in the antibody titer measurement to verify wells containing cells producing antibodies.

In secondary screening, 50 µL of the culture supernatant from only the wells positive in the primary screening were dispensed to use as a primary antibody. ELISA using the fibrin plate and the fibrinogen plate was performed as in the antibody titer measurement to verify wells containing cells producing insoluble fibrin-specific antibodies. The wells that were positive in the secondary screening were subjected to colony picking using 200 µL-scaled Tip Yellow (Watson).

The tip was pressed to a colony, and 5 µL of the colony were sucked up and seeded in a fresh Costar 96-Well Cell Culture Plate.

In tertiary screening, 50 µL of the culture supernatant from the wells in which the colony was seeded were dispensed to use as a primary antibody. ELISA using the fibrin plate and the fibrinogen plate was performed as in the antibody titer measurement. The cells in the wells that were positive in the tertiary screening were subjected to limiting dilution.

In quaternary screening, 50 µL of the culture supernatant from only wells of a single cell were dispensed to use as a primary antibody. ELISA using the fibrin plate and the fibrinogen plate was performed as in the antibody titer measurement to select cells producing insoluble fibrin-specific antibodies.

Clone 99-5 was obtained from a mouse immunized with a peptide having the amino acid sequence of SEQ ID NO: 26. Clone 1101 was obtained from a mouse immunized with a peptide having the amino acid sequence of SEQ ID NO: 27. The "clone 99-5" may be referred to as simply "clone 99".

Example 2: Characteristic Analysis of the Resulting Monoclonal Antibodies

In this example, the affinity of an antibody was verified by ELISA and surface plasmon resonance (SPR).

(1) Verification of Affinity by ELISA

In advance of the ELISA, an antigen-immobilized plate was prepared. Fibrinogen from human plasma (SIGMA) was dissolved in TBS (pH 8.5) to produce a 20 µg/mL fibrinogen solution. The solution was added to a 96-well immunoplate at 50 µL/well and was left to stand at 4° C. overnight to prepare a fibrinogen plate. Thrombin diluted to 0.05 NIH U/mL with a thrombin diluent [7 mM L-cysteine (FUJIFILM Wako Pure Chemical Corporation), 1 mM $CaCl_2$ (FUJIFILM Wako Pure Chemical Corporation), TBS (pH 8.5)] was added to the fibrinogen plate at 100 µL/well and was incubated at 37° C. for 2 hours to prepare a fibrin plate. The plate on which each antigen was immobilized was washed with 200 µL of PBS-T (PBS, 0.5% (v/v) Tween 20) three times, and 200 µL of a blocking solution [PBS-T, 1% (w/v) BSA] were added to each well, followed by being left to stand at room temperature for 1 hour for blocking. The samples serially diluted with PBS were added to the plate at 50 µL/well and were left to stand at room temperature for 1 hour. The solutions were discarded, and the plate was washed with PBS-T three times. A secondary antibody diluted to 0.3 µg/mL with the blocking solution was added to the plate at 50 µL/well, followed by being left to stand at room temperature for 30 minutes. As the secondary antibody, polyclonal rabbit anti-mouse immunoglobulins/HRP (Dako) and polyclonal rabbit anti-rat immunoglobulins/HRP (Dako) were used properly according to the sample. The solutions were discarded, the plate was washed with PBS-T three times, and a chromogenic substrate solution was added to the plate at 100 µL/well, followed by a reaction at room temperature for 10 minutes. The reaction was stopped by adding 30 µL of 2N $H_2SO_4$ to each well. The absorbance at a wavelength of 450 nm was measured with a Spectra Max paradigm (Molecular Devices).

The results were as shown in FIG. 1. As shown in FIG. 1, the antibodies obtained from clone 99 and clone 1101, which were newly prepared in the above-described example, were insoluble fibrin-specific antibodies that bind more strongly to insoluble fibrin than to fibrinogen. In addition, the antibodies more strongly reacted with fibrin than the antibody obtained from clone 102-10 obtained in WO 2016/167227.

(2) Verification of Affinity by SPR

When an antigen is insoluble, although SPR is not suitable for verifying the affinity of the antigen, measurement by SPR was performed as reference for comparing relative affinity levels between antibodies.

The affinity of an antibody to insoluble fibrin was calculated based on analysis by surface plasmon resonance (SPR) using Biacore T200 (GE Healthcare) to evaluate the intermolecular interaction of the antibody. The buffer used in the flow channel was HBS-N buffer (GE Healthcare) The peptide of the epitope site of 102-10 (see WO 2016/167227) was diluted to 1 µg/mL with 10 mM sodium acetate, pH 5.5 (GE Healthcare) and was immobilized on a sensor chip (Biacore sensor chip CM5, GE Healthcare). The immobilization was performed using an amine coupling kit (BR-1000-50, GE Healthcare) and setting the immunization amount to 90 RU. Subsequently, an antigen-antibody reaction was performed using an antibody diluted to 48.875, 93.75, 187.5, 375, 750, and 1500 nM with 1× HBS-N buffer by a multi cycle kinetics method under conditions shown in Table 1. After the measurement, analysis using BIA evaluation (GE Healthcare) was performed to determine the KD value, kd value, and ka value.

TABLE 1

Conditions for SPR

Conditions for measurement on sample

| | |
|---|---|
| contact time | 120 sec |
| flow rate | 30 µl/min |
| dissociation time | 180 sec |

Conditions for regeneration

| | |
|---|---|
| Reagent | 10 mM Glycine-HCl pH 1.5 |
| contact time | 60 sec |
| flow rate | 30 µl/min |
| stabilization period | 30 sec |

The results were as shown in Table 2.

TABLE 2

Affinity of each clone-producing antibody to epitope by SPR

| Clone No. | Binding rate constant ka (1/Ms) | Dissociation rate constant kd (1/s) | Affinity KD (M) |
|---|---|---|---|
| 99-5 | $1.80 \times 10^4$ | $5.85 \times 10^{-4}$ | $3.26 \times 10^{-8}$ |
| 3435 | $1.63 \times 10^4$ | $3.68 \times 10^{-4}$ | $2.25 \times 10^{-8}$ |
| 1101 | $9.37 \times 10^4$ | $3.25 \times 10^{-3}$ | $6.68 \times 10^{-8}$ |
| 102-10 | $3.77 \times 10^4$ | $1.75 \times 10^{-3}$ | $4.64 \times 10^{-8}$ |

Example 3: Verification of Accumulation of Antibody to Cancer Using Pancreatic Cancer Subcutaneous Implantation Model In this example, LSL-Kras$^{G12D/+}$ and Ptf1a-Cre provided by Y. Kawaguchi, C. Wright, and D. Tuveson and LSL-Trp53$^{R172H/+}$ provided by National Cancer Institute at Frederick were crossed to produce p53/p48/K-Ras triple mutant mice (pancreatic cancer mouse model), and a triple mutant mouse-derived pancreatic cancer cell line was established. Accordingly, in vivo imaging was performed using the cell line. It has been reported that the triple mutant mice imitate development of human pancreatic cancer. The pancreatic cancer cell line was cultured in 500 mL of a RPMI 1640 (FUJIFILM Wako Pure Chemical Corporation) medium supplemented with 100 mL of inactivated fetal bovine serum (FBS, Gibco) and 10 mL of 100 units/mL Penicillin, 100 µg/mL Streptomycin, and 250 ng/mL Amphotericin B (FUJIFILM Wako Pure Chemical Corporation). The culture supernatant was then removed. The cells were washed with PBS (Invitrogen), and 2 mL of Trypsin-EDTA [0.25% (w/v) trypsin-1.0 mmol/L ethylenediaminetetraacetic acid-4Na Solution with Phenol Red, FUJIFILM Wako Pure Chemical Corporation] was added thereto. The cells were detached by pipetting and placed in a 15-mL tube (Corning Incorporated), followed by centrifugation with a centrifuge (Universal centrifuge 5800, KUBOTA Corporation Co., Ltd.) at 270×g for 3 minutes at 4° C. The supernatant was removed, and the precipitate was resuspended in 10 mL of PBS, followed by centrifugation at 270×g for 3 minutes at 4° C. After repeating this procedure three times, the concentration was adjusted to $2 \times 10^6$ cells/50 µL with PBS, and the cell solution was subcutaneously injected to 5-week old BALB/c Slc nu/nu mice (Japan SLC, Inc.) at 50 µL per mouse from the left foot base. After one month, an Alexa 647-labeled anti-insoluble fibrin antibody or a control antibody was administered at 300 µg per mouse from the tail vein. The control used was InVivoMAb Mouse IgG1 Isotype control (Bio X Cell). The mice were photographed with an in vivo living-body observation system OV110 (Olympus Corporation) one hour after the administration and on the first, third, fifth, and seventh days after the administration.

Figure 2:
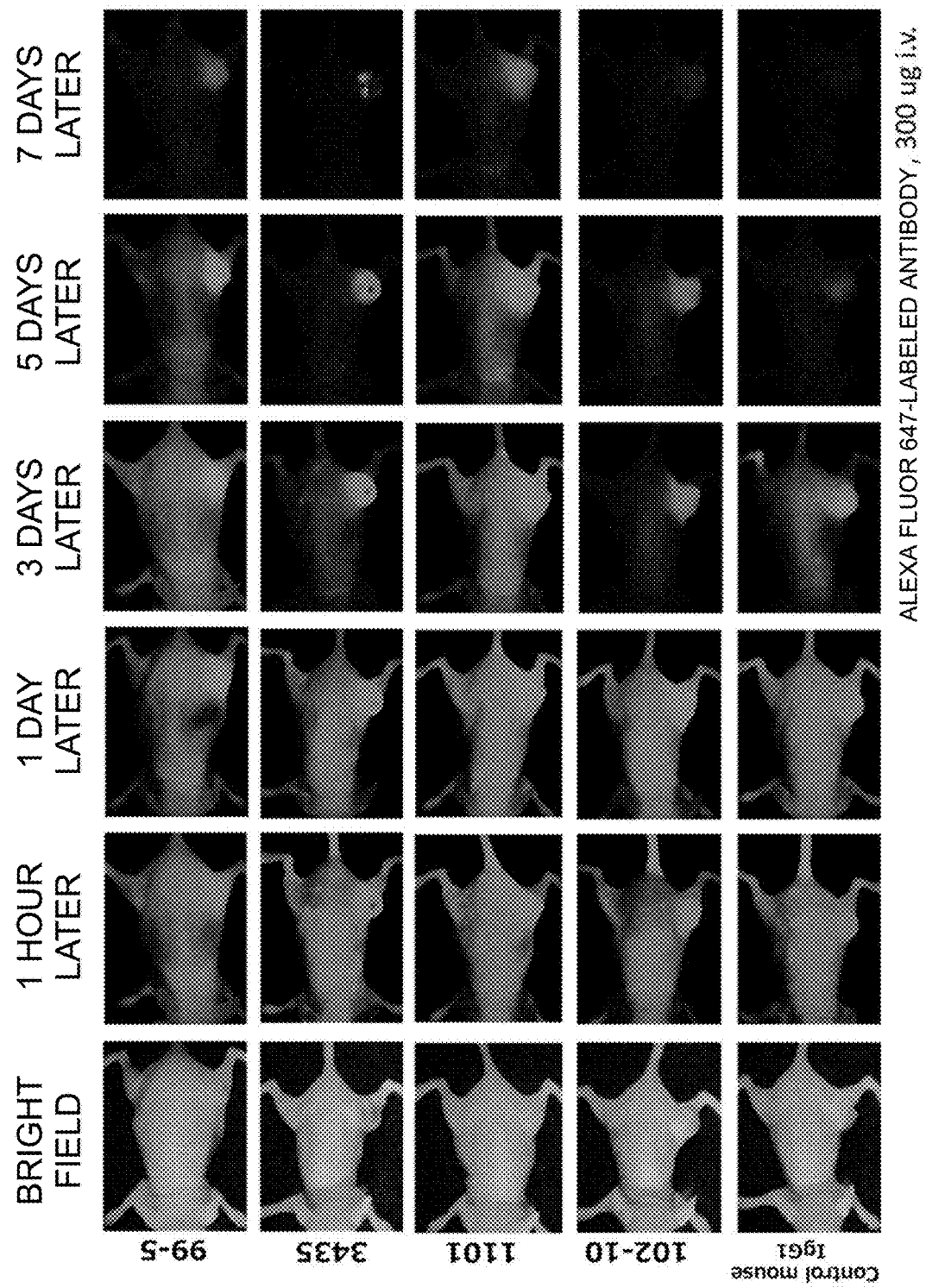
FIG. 2 shows that monoclonal antibodies specific to insoluble fibrin obtained by the present invention accumulate at tumor-forming sites.

The results were as shown in FIG. 2. As shown in FIG. 2, it was revealed from the imaging that accumulation of the resulting insoluble anti-insoluble fibrin antibodies (in particular, 1101 and 99) to cancer is high.

Subsequently, a surgically removed tumor was embedded in an OCT compound (Sakura Finetek Japan Co., Ltd.) and frozen to produce thin-layer sections of 6 µm. The thin-layer sections were air-dried with a dryer for 45 minutes and were then fixed with cooled acetone (FUJIFILM Wako Pure Chemical Corporation) for 10 minutes. After washing with PBS, nuclear staining with Mayer's Hematoxylin (Muto Pure Chemicals Co., Ltd.) was performed for 2 minutes. After washing with running water for 10 minutes, the cytoplasm was stained with eosin alcohol (Muto Pure Chemicals Co., Ltd.) diluted three-fold with 100% ethanol. After washing with running water, immersion in 100% ethanol for 3 minutes and immersion in xylene (FUJIFILM Wako Pure Chemical Corporation) for 3 minutes were each repeated three times for dehydration and permeation. Finally, the sections were mounted with Mount-Quick (Daido Sangyo Co., Ltd.).

Surgically removed tumor was embedded in an OCT compound (Sakura Finetek Japan Co., Ltd.) and frozen to produce thin-layer sections of 6 µm. The thin-layer sections were air-dried with a dryer for 45 minutes and were then fixed with cooled acetone (FUJIFILM Wako Pure Chemical Corporation) for 10 minutes. After washing with PBS, the sections were immersed in 0.3% (v/v) $H_2O_2$ for 20 minutes for endogenous peroxidase inhibition. After washing with PBS for 5 minutes three times, blocking with a blocking solution [5% (w/v) skimmed milk (Difco), PBS] was performed for 30 minutes. To the sections, 200 µL of a HRP-labeled antibody diluted to 1 µg/mL with the blocking solution was dropwise added, followed by a reaction at 4° C. overnight. After washing with PBS for 5 minutes three times, an enzyme-substrate reaction with 3,3'-diaminobenzidine tetrahydrochloride (Dako) was performed. Subsequently, washing with sterile distilled water was performed for 3 minutes, and nuclear staining with Mayer's Hematoxylin (Muto Pure Chemicals Co., Ltd.) was performed for 2 minutes. After washing with running water for 10 minutes, immersion in 100% ethanol for 3 minutes and immersion in xylene (FUJIFILM Wako Pure Chemical Corporation) for 3 minutes were each repeated three times for dehydration and permeation. Finally, the sections were mounted with Mount-Quick (Daido Sangyo Co., Ltd.).

Example 4: In Vitro Anticancer Activity

In this example, an antibody-drug conjugate (ADC) in which monomethyl auristatin E (MMAE) was linked to the resulting insoluble fibrin-specific antibody was produced, and the anticancer activity of the ADC was evaluated.

Figure 3:
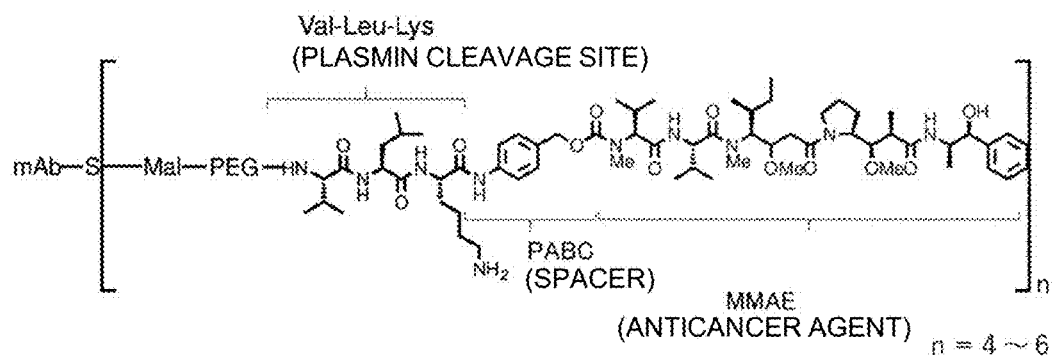
FIG. 3 shows especially a drug portion and a linker portion of an antibody-drug conjugate produced by the present invention.

As the ADC, an ADC having the structure shown in FIG. 3 was synthesized. In this ADC, MMAE as the anticancer agent was linked to a monoclonal antibody (mAb). In the ADC, the antibody and MMAE were linked to each other via a polyethylene glycol (PEG) spacer and a plasmin cleavage site, Val-Leu-Lys. Accordingly, the ADC is cleaved in the presence of plasmin, and the MMAE is liberated from the antibody.

The ADC was specifically synthesized as follows.

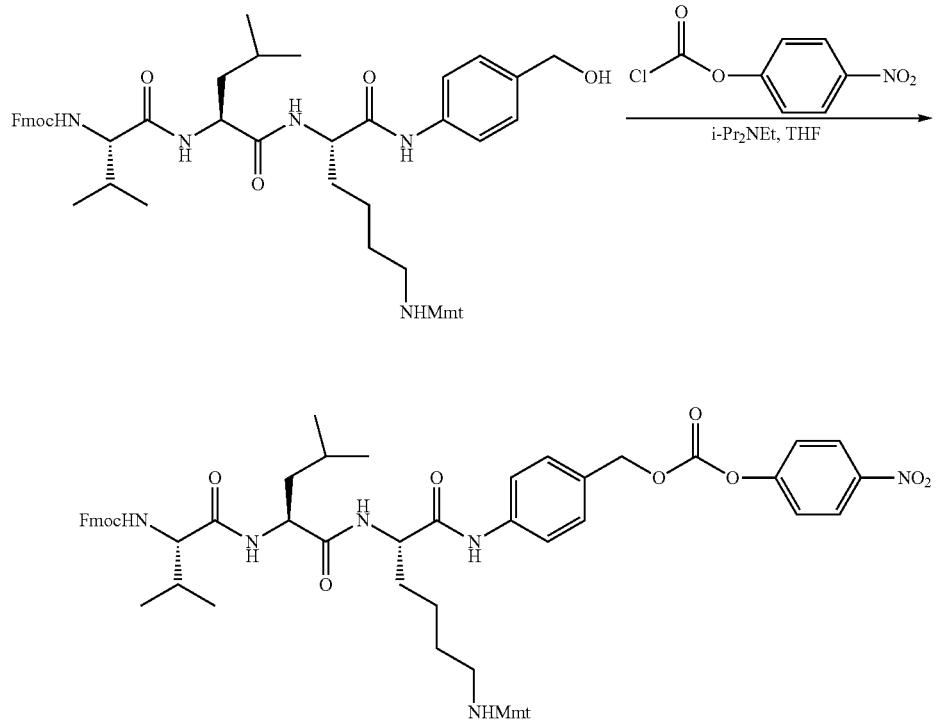

DIPEA (0.54 mL, 3.10 mmol) and p-nitrophenyl chloroformate (472 mg, 1.55 mmol) were added to a DMF (2 mL) solution containing Fmoc-Val-Leu-Lys(Mmt)-aminobenzyl alcohol (0.74 g, 0.773 mmol) at 0° C., followed by stirring at room temperature for 12 hours. The reaction solution was stopped with a saturated ammonium chloride aqueous solution, followed by extraction with chloroform. The extraction layer was washed with a saturated saline solution, dried over $Na_2SO_4$, and concentrated under reduced pressure. The residue was purified by silica gel chromatography ($CHCl_3$:MeOH=95:5 to 9:1) to give Fmoc-Val-Leu-Lys(Mmt)-OP-ABC-p-nitrophenyl carbonate as a colorless amorphous product.

$^1$H NMR (400 MHz, $CDCl_3$): d 8.01 (br, 1H), 7.76 (br, 1H), 7.05-7.60 (m, 13H), 6.78 (d, J=6.8 Hz, 2H), 5.49 (br, 1H), 5.25 (br, 1H), 4.94 (br, 1H), 4.77 (s, 2H), 4.04 (s, 3H), 4.00-4.85 (m, 3H), 3.75 (s, 3H), 3.55-3.90 (m, 2H), 3.26 (d, J=19.6 Hz, 1H), 3.00 (d, J=19.6 Hz, 1H), 2.32 (br, 1H), 1.26 (s, 3H), 1.05-2.25 (m, 15H), 0.70-1.05 (m, 12H); HRMS (ESI-MS): calcd for $C_{72}H_{85}N_6O_{17}$: 1305.5971 $[M+H]^+$; found 1305.5935.

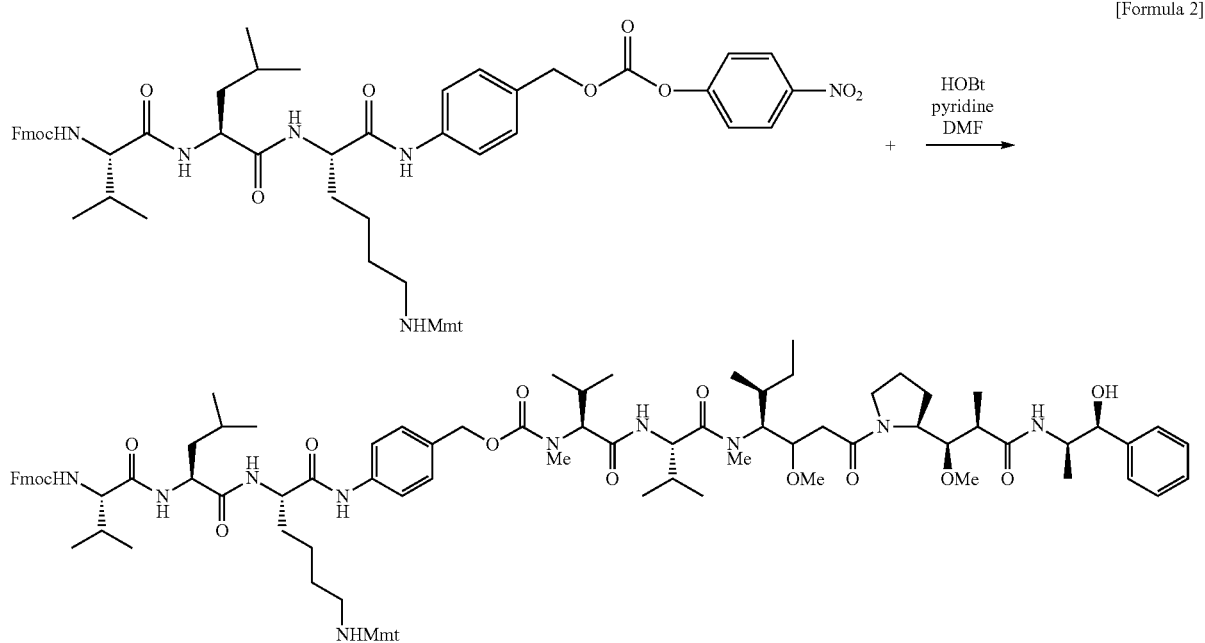

MMAE (14.1 mg, 0.0197 mmol) was added to a pyridine (80 mL)/DMF (0.4 mL) solution containing p-nitrophenyl carbonate body (33.2 mg, 0.0296 mmol) and HOBt (0.5 mg, 0.0039 mmol) at 0° C. The reaction solution was stirred at room temperature for 10 hours and was then purified by direct LH20 (chloroform:methanol=1:1) to give Fmoc-Val-Leu-Lys(Mmt)-OPABC-MMAE (22.7 mg, 68%) as a colorless amorphous product.

MS (MALDI-TOFMS) calcd for $[C_{99}H_{132}N_{10}O_{15}+K]^+$ 1739.95; found 1741.37.

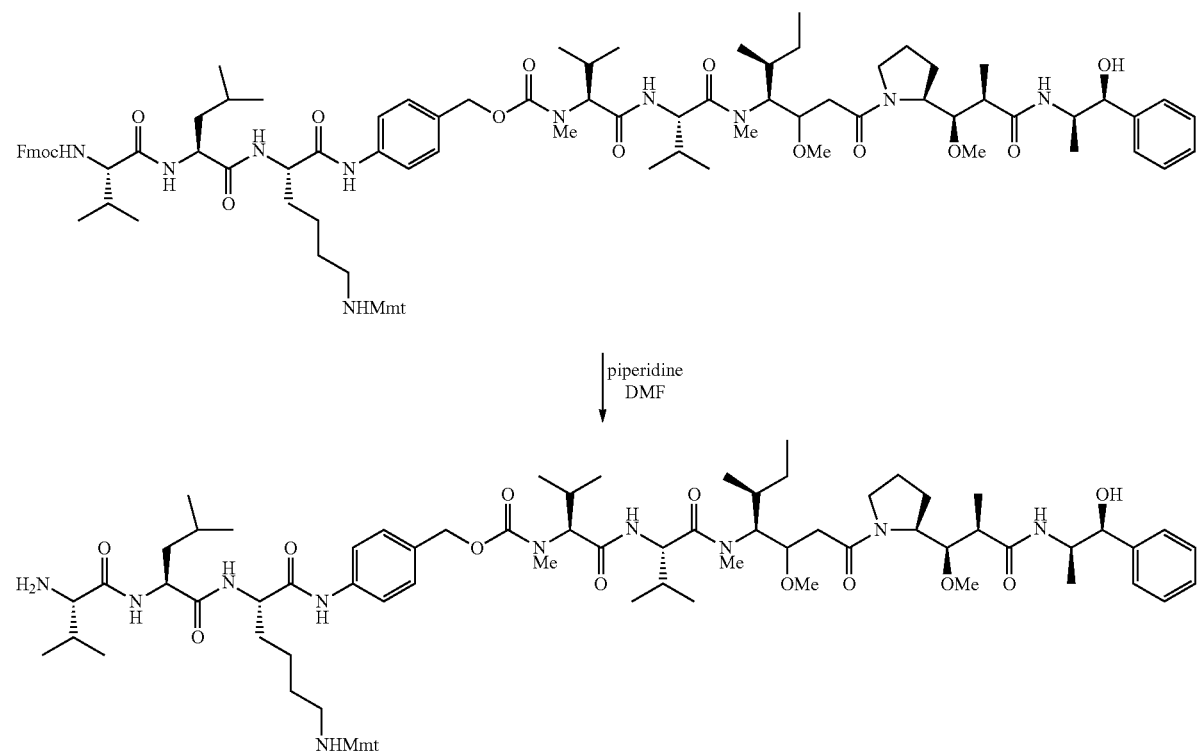

Piperidine (110 mL, 1.10 mmol) was added to a DMF (3 mL) solution containing Fmoc-Val-Leu-Lys(Mmt)-OPABC-MMAE (626 mg, 0.368 mmol), followed by stirring at room temperature for 40 minutes. The reaction solution was purified by LH20 (chloroform:methanol=1:1) and HPLC (YMC T4000 10.0 mL/min, CHCl$_3$: MeOH=4:1, 254 nm) to give H-Val-Leu-Lys(Mmt)-OPABC-MMAE (458 mg, 84%) as a colorless amorphous product.

MS (MALDI-TOFMS) calcd for $[C_{94}H_{122}N_{10}O_{13}+K]^+$ 1519.02; found 1519.65.

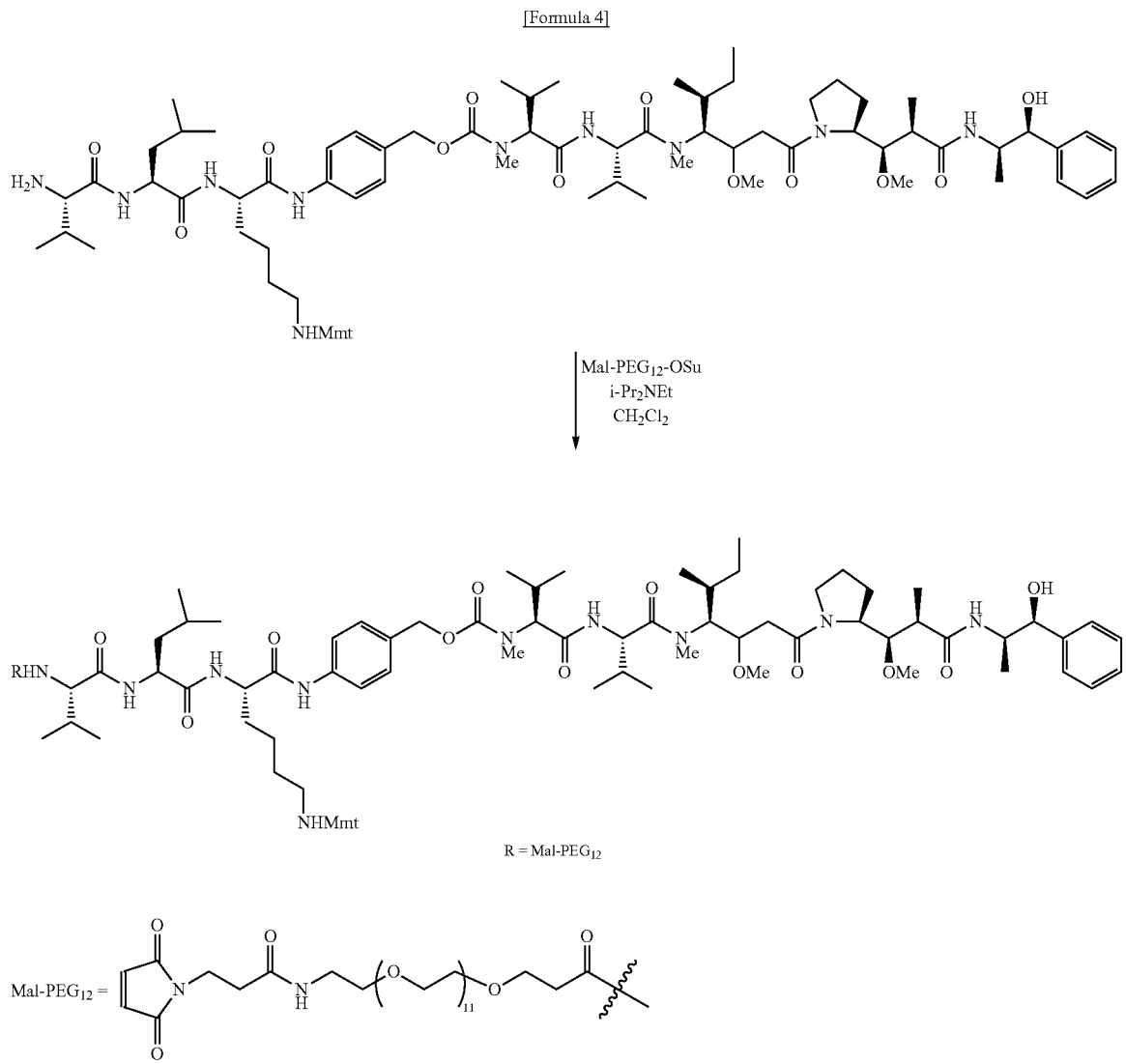

[Formula 4]

A methylene chloride solution (1 mL) containing DIPEA (160 mL, 0.927 mmol) and Mal-PEG$_{12}$-OSu (295 mg, 0.340 mmol) was added to a methylene chloride solution (2 mL) containing H-Val-Leu-Lys(Mmt)-OPABC-MMAE (458 mg, 0.309 mmol) at 0° C. The reaction solution was stirred at room temperature for 22 hours, followed by purification by LH20 (chloroform:methanol=1:1) and molecular sieve recycling HPLC (YMC T4000 10.0 mL/min, CHCl$_3$, 254 nm) to give Mal-PEG$_{12}$-Val-Leu-Lys(Mmt)-OPABC-MMAE (498 mg, 72%) as a colorless amorphous product.

MS (MALDI-TOFMS) calcd for $[C_{118}H_{180}N_{12}O_{29}+K-Mmt]^+$ 1997.51; found 1999.49.

[Formula 5]

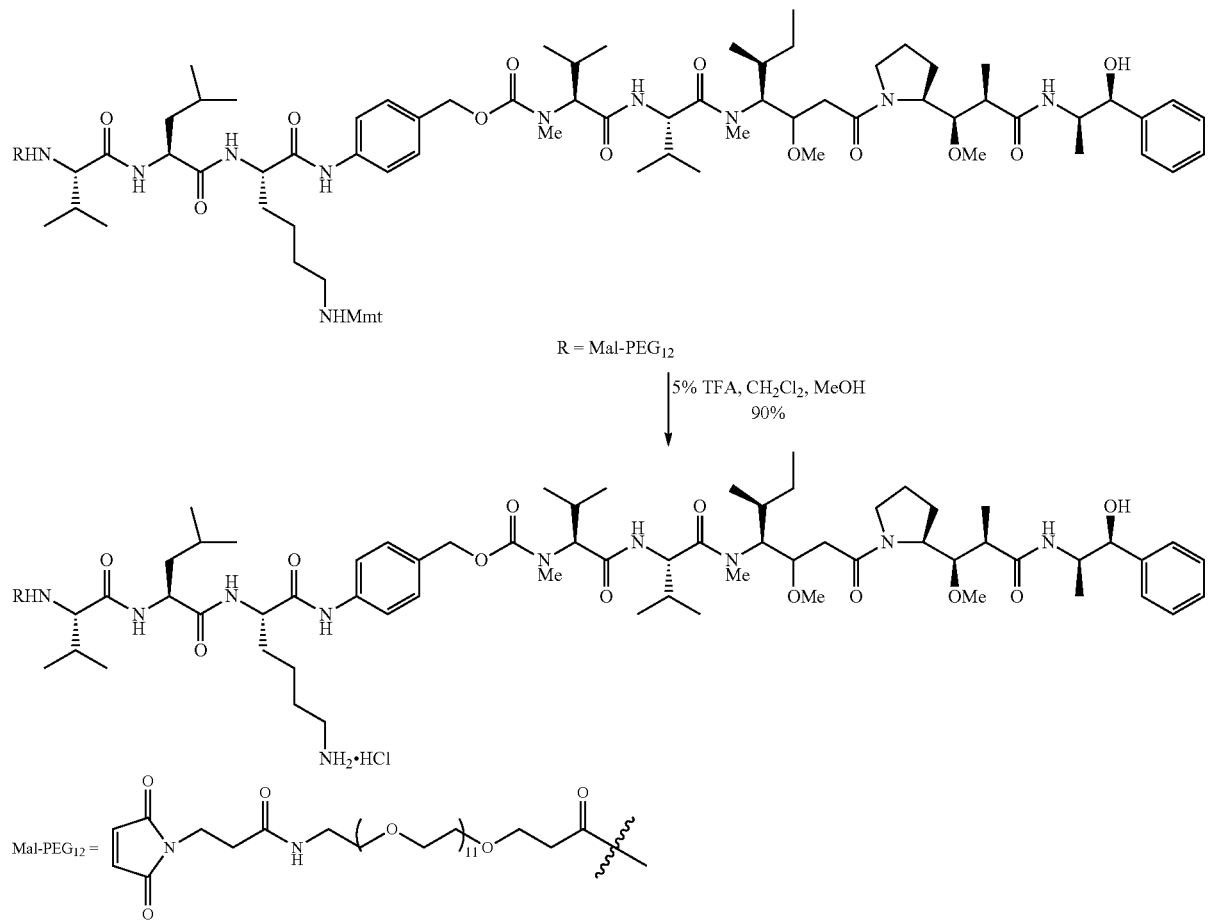

Mal-PEG$_{12}$-Val-Leu-Lys(Mmt)-OPABC-MMAE (498 mg, 0.223 mmol) was dissolved in a 5% TFA methylene chloride solution (2 mL), and methanol (50 mL) was added thereto, followed by stirring at room temperature for 1 hour. The reaction solution was purified by direct LH20 (chloroform:methanol=1:1) and then HPLC (YMC T4000, 10.0 mL/min, CHCl$_3$, 254 nm)) to give Mal-PEG$_{12}$-Val-Leu-Lys-OPABC-MMAE (440 mg, 90%) as a colorless amorphous product.

MS (MALDI-TOFMS) calcd for $[C_{98}H_{164}N_{12}O_{28}+K]^+$ 1997.51; found 1998.31.

Subsequently, a fibrin plate was produced. A 25 mg/mL fibrinogen solution (5 μL) was added to a 96-well plate for cell culture along the wall surface. A thrombin solution (1 μL) was added to each well, followed by centrifugation at 40×g at 4° C. for 1 minute. After a reaction at 37° C. for 2 hours, the plate was stored at 4° C. until use.

5-11 Cell line (TG mouse-derived pancreatic cancer cells) was seeded on the resulting fibrin-coated plate at 2000 cells/well, followed by culturing at 37° C. overnight. As the culture medium, a RPMI medium containing 10% FBS was used.

A dilution series with final concentrations of 0 to 25 nM (in terms of MMAE) of the ADC was prepared.

The final concentrations of plasminogen, tPA, and α2-antiplasmin were adjusted to approximately the same concentrations as those in normal plasma, i.e., about 1500 nM, about 0.3 nM, and about 1000 nM, respectively.

The culture solution was removed from the fibrin plate, and 90 μL of the solution containing plasminogen, tPA, and α2-antiplasmin were added thereto, and 10 μL of a dilution series of ADC (in the drawing, referred to as "Fbn-ADC") were then added thereto. As controls, an insoluble fibrin antibody alone (in the drawing, referred to as "IgG") and an ADC (in the drawing, referred to as "Control-ADC") in which an anti-4M-Tag antibody (control IgG) was used as the antibody in FIG. 3 were used. After incubation at 37° C. for 72 hours, the culture solution was removed. A reaction solution prepared by mixing CCK-8 (Dojindo Laboratories) and a culture solution at a ratio of 1:10 was added to the plate, followed by incubation at 37° C. for 3 hours. The IC$_{50}$ was calculated from an optical density curve determined at A450.

Figure 4:
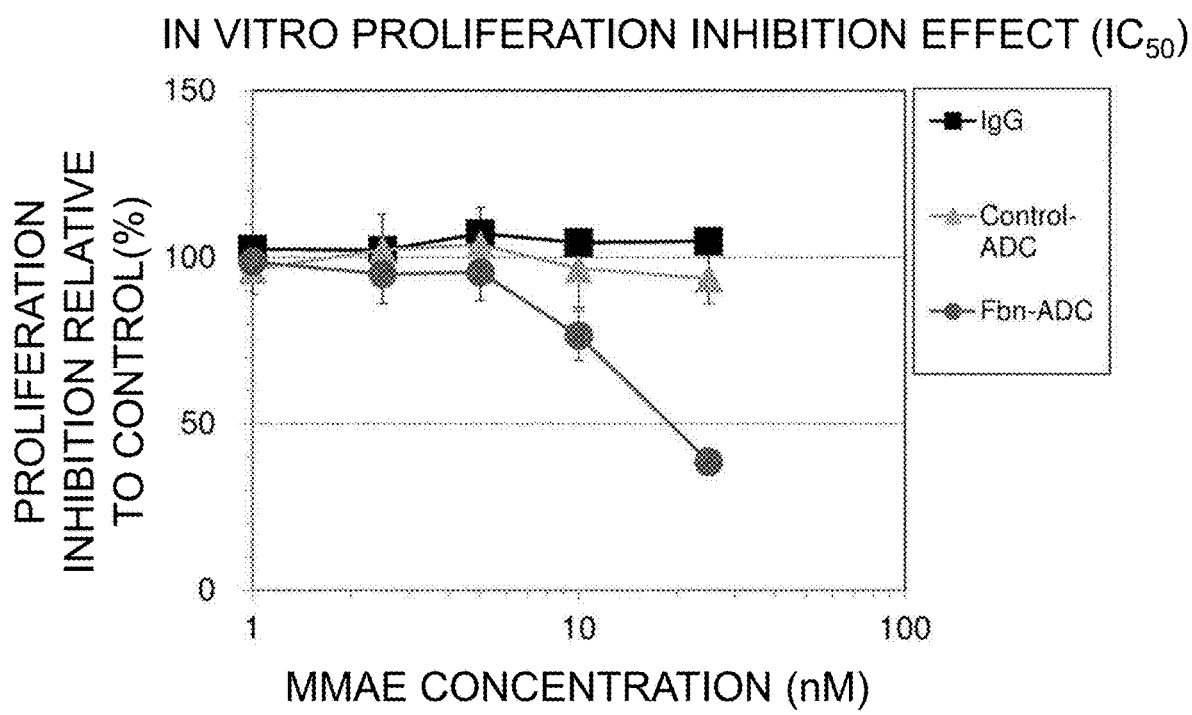
FIG. 4 shows the results of verification of in vitro anticancer activity of the antibody-drug conjugate produced by the present invention.

The results were as shown in FIG. 4. The ADC of the insoluble fibrin-specific antibody showed a cancer cell proliferation inhibition effect, but in the control, no significant tumor proliferation inhibition effect was observed. This result demonstrates that the insoluble fibrin-specific antibody-ADC bound to the fibrin coated on a plate and that the linker is then cleaved by plasmin to release MMAE to kill tumor cells. The IC$_{50}$ of the insoluble fibrin-specific antibody-ADC was 19 nM.

Example 5: In Vivo Anticancer Activity of the Insoluble Fibrin-Specific Antibody-ADC The present inventors have set up a hypothesis that in vivo proliferation of cancer damages the blood vessels surrounding the cancer to cause bleeding and consequently insoluble fibrin accumulates near the tumor for arresting the bleeding and that an anticancer agent can be delivered to the vicinity of the cancer by using an antibody that binds to the accumulated insoluble fibrin. The present inventors also have created a concept of a new anticancer agent in which a plasmin cleavage site is inserted into the linker of an ADC, and thereby the ADC reached insoluble fibrin is cleaved and further releases the anticancer agent insoluble fibrin dependently by plasmin activated on the insoluble fibrin. The present inventors have set up a hypothesis that the ADC consequently accumulates insoluble fibrin dependently and releases the anticancer agent to enhance cancer specificity.

The therapeutic effect by the ADC against a model having spontaneous pancreatic cancer (spontaneous pancreatic cancer model) in the P53/K-ras/P48 triple mutant mice was verified. The insoluble fibrin-specific antibody-ADC (0.3 mg (in terms of MMAE)/kg weight/3 to 4 days (i.e., 20 mg (in terms of ADC)/kg weight/3 to 4 days) was administered to the model, and a Kaplan-Meier curve was determined. The significance level in a Logrank test was set to 0.05. As the control ADC (in the drawing, referred to as "Control-ADC"), anti-4M-Tag antibody was used.

Figure 5:
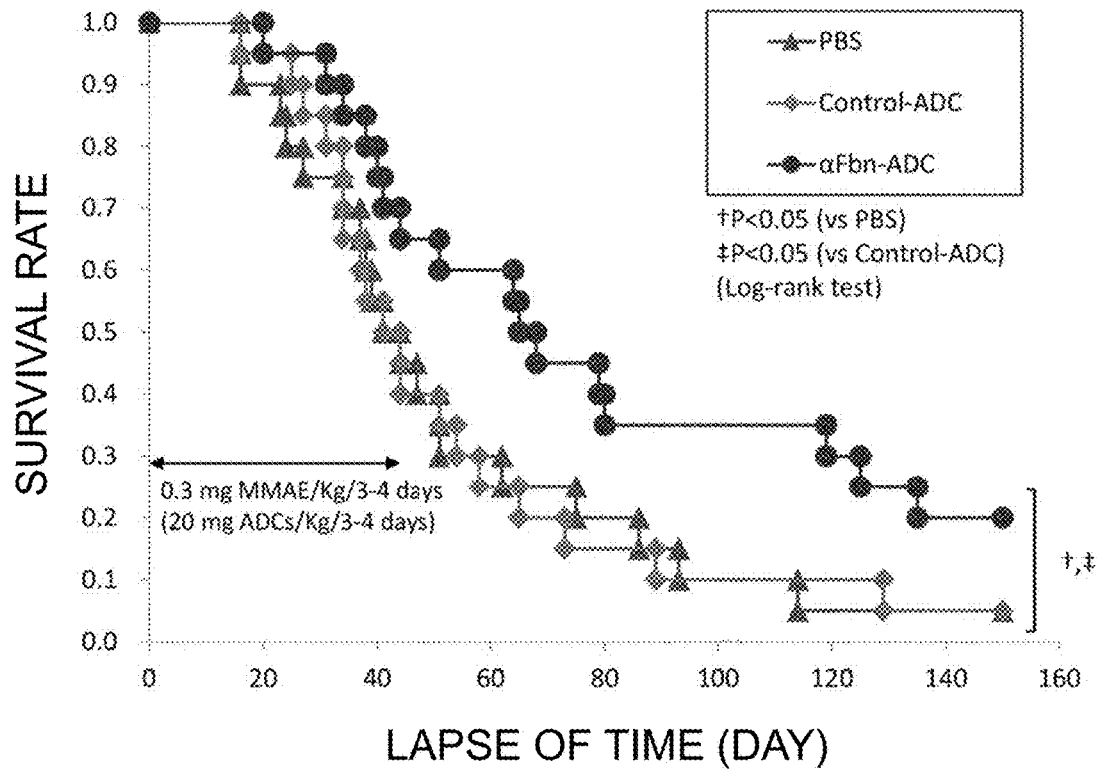
FIG. 5 shows a Kaplan-Meier curve of an antibody-drug conjugate produced by the present invention for a spontaneous pancreatic cancer model.

The results were as shown in FIG. 5. As shown in FIG. 5, the ADC (in the drawing, referred to as "αFbn-ADC") significantly improved the survival rate of the spontaneous pancreatic cancer model compared to the control. Consequently, it was proved that the above-described hypotheses are correct.

Example 6: Anticancer Activity of the Insoluble Fibrin-Specific Antibody-ADC in Subcutaneous Tumor Model with Fibrin Deposition In this example, a cell line was established from the triple mutant-derived spontaneous pancreatic cancer, and a subcutaneous tumor model obtained by subcutaneous implantation of the cell line was used for verification of the anticancer activity of the insoluble fibrin-specific antibody-ADC.

The cell line established from the triple mutant-derived spontaneous pancreatic cancer was named as 5-11. $5 \times 10^5$ cells of 5-11 were subcutaneously implanted into BALB/C nude mice to produce a subcutaneous implantation model. This subcutaneous implantation model had fibrin deposition subcutaneously. The resulting subcutaneous tumor model was administered with the insoluble fibrin-specific antibody-ADC (0.3 mg (in terms of MMAE)/kg weight/3 to 4 days (i.e., 20 mg (in terms of ADC)/kg weight/3 to 4 days)), and the change in the tumor volume increase rate was observed. The significance level in comparison by ANOVA was set 0.01.

Figure 6A:
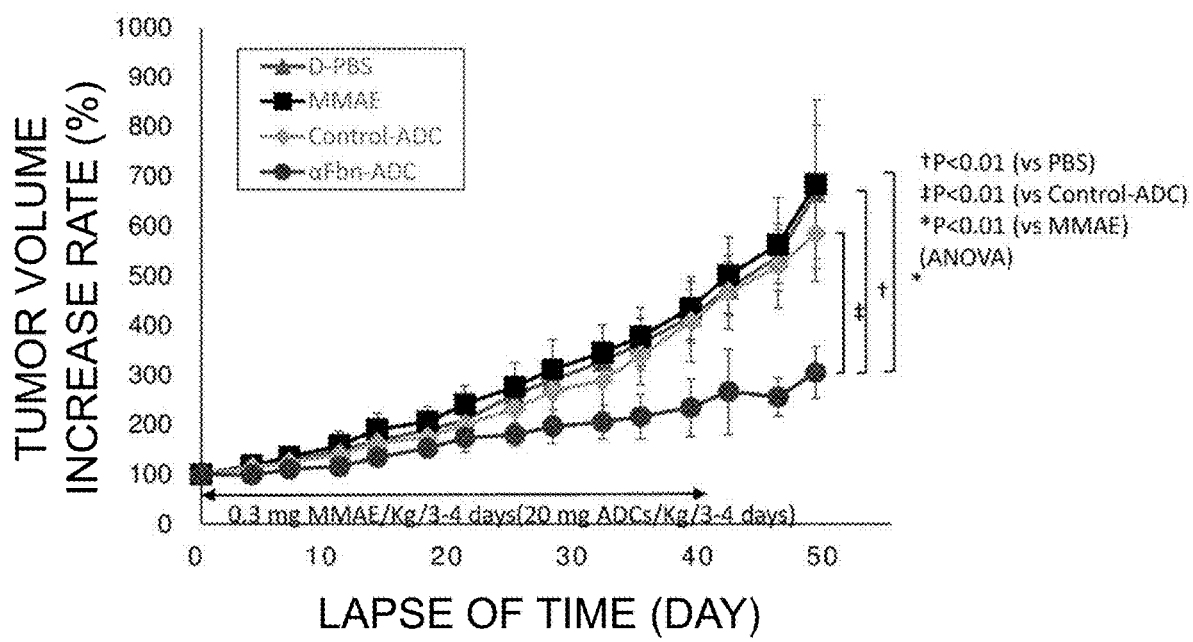
FIG. 6A shows an effect of suppressing an increase in tumor volume in tumor subcutaneous implantation mice by the antibody-drug conjugate produced by the present invention.

The results were as shown in FIG. 6A. As shown in FIG. 6A, the ADC (in the drawing, referred to as "(Fbn-ADC") significantly suppressed the increase in tumor volume compared to the control.

Figure 6B:
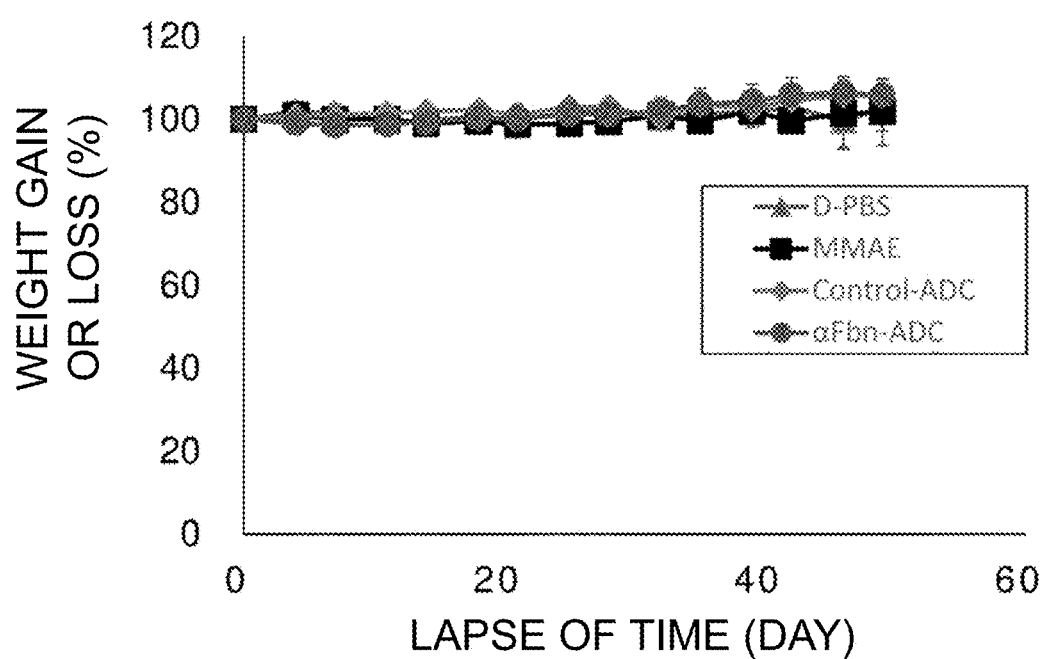
FIG. 6B shows changes with time in weight of the mice observed in FIG. 6A.

Changes in body weight over time in subcutaneous implantation model were as shown in FIG. 6B. As shown in FIG. 6B, there was no significant increase or decrease in weight, which revealed that the ADC of the present invention can be a therapeutic agent with few side effects.

Subsequently, the antitumor effect was compared to the case of a linker not having the plasmin cleavage sequence.

44As3 was seeded on the resulting fibrin-coated plate and not coated plate at 3000 cells/well, followed by culturing at 37° C. overnight. As the culture medium, a RPMI medium containing 10% FBS was used.

Dilution series with final concentrations of 0 to 3 nM (in terms of MMAE) of an ADC having a cathepsin linker (containing valine-citrulline) and an ADC having a plasmin linker were prepared.

The final concentrations of plasminogen, tPA, and α2-antiplasmin were adjusted to approximately the same concentration ratios as those in normal plasma, i.e., about 150 nM, about 0.03 nM, and about 100 nM, respectively.

The culture solution was removed from each plate, and 90 μL of the solution containing plasminogen, tPA, and α2-antiplasmin and then 10 μL of a dilution series of ADC were added to each plate. After incubation at 37° C. for 72 hours, the culture solution was removed. A reaction solution prepared by mixing CCK-8 (Dojindo Laboratories) and a culture solution at a ratio of 1:10 was added to each plate, followed by incubation at 37° C. for 2 hours. The $IC_{50}$ was calculated from an optical density curve determined at A450.

Figure 7:
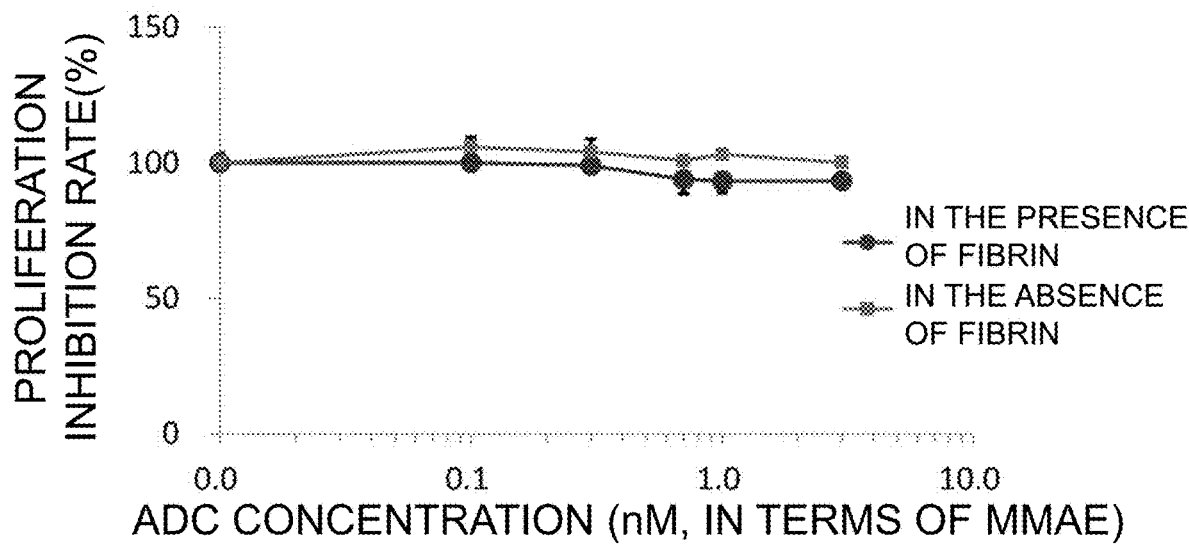
FIG. 7 shows cytostatic activities of an ADC having a plasmin linker having a plasmin cleavage site or an ADC having a cathepsin linker not having a plasmin cleavage site but having a cathepsin cleavage site instead.
Figure 7:
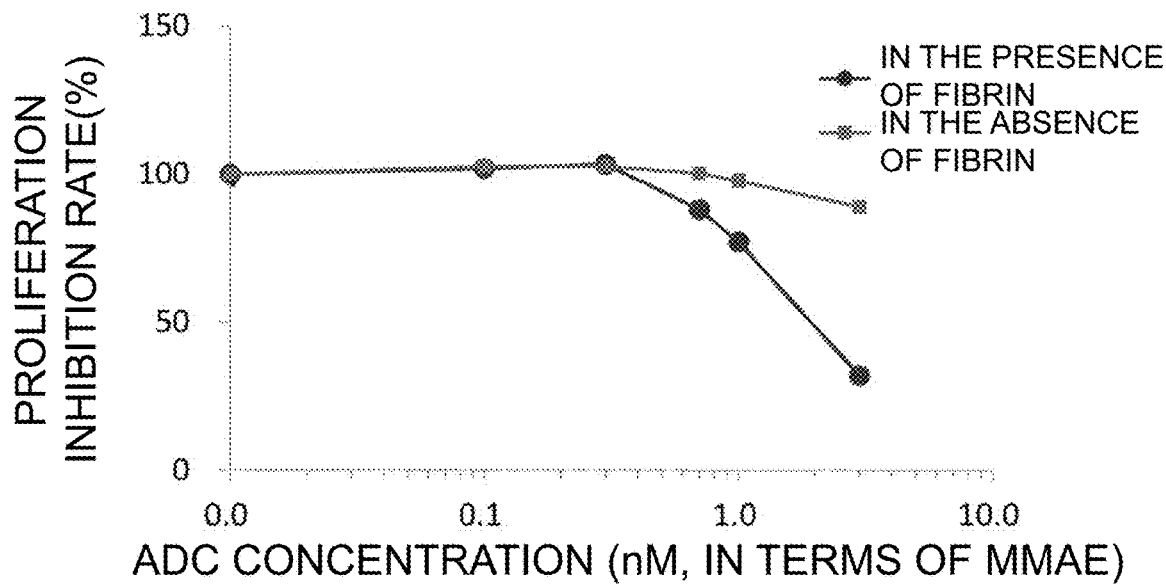

The results were as shown in FIG. 7. As shown in FIG. 7, the ADC having a plasmin cleavage site (in the drawing, referred to as "plasmin linker") clearly showed a cell proliferation inhibition effect on tumor cells, but the ADC in which the linker having a plasmin cleavage site was replaced by a linker having a cathepsin cleavage site (in the drawing, referred to as "cathepsin linker") showed almost no cell proliferation inhibition effect on tumor cells.

Figure 8:
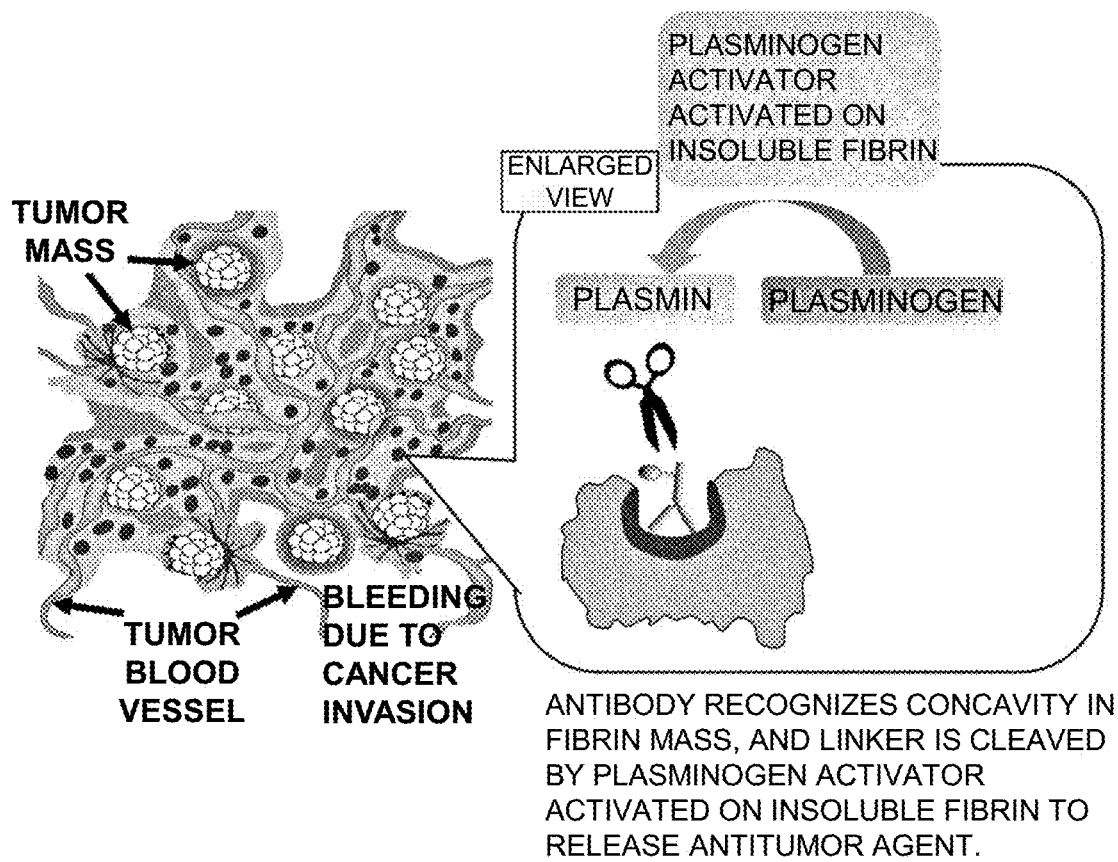
FIG. 8 shows a presumed action mechanism of an antibody-drug conjugate produced by the present invention.

From the above-described results, as shown in FIG. 8, the action mechanism of the ADC of the present invention is inferred as follows: an anti-insoluble fibrin antibody-cytotoxic agent conjugate including a linker having a plasmin cleavage site is delivered by blood circulation to the vicinity of cancer where insoluble fibrin accumulates, the linker site is cleaved by plasmin near fibrin, and the cytotoxic agent is released to the vicinity of the cancer. Consequently, the cancer comes into contact with the cytotoxic agent.

Cancer with a higher degree of malignancy is more invasive to tissues. When cancer invades a blood vessel, bleeding occurs, and insoluble fibrin is then formed at the bleeding site. The ADC of the present invention is inferred to have especially high effectiveness on such cancer with a high degree of malignancy. In addition, it is inferred that the ADC similarly shows an anticancer activity even if another insoluble fibrin-specific antibody is used.

Example 7: Sequence Analysis of Antibody $5 \times 10^5$ cells were transferred from a 100-mm dish (Corning Incorporated) to a 15-mL tube, followed by centrifugation at 270×g for 3 minutes at 4° C. After removing the supernatant, 1 mL of RNAiso Plus (Takara Bio Inc.) was added to the tube. The cells were transferred to an Eppendorf and were vortexed. Subsequently, the cell suspension was left to stand at room temperature for 5 minutes, followed by extraction of total RNA with an RNeasy Mini Kit (Qiagen). Chloroform (200 μL, FUJIFILM Wako Pure Chemical Corporation) was added to the cell suspension, vortexed for 30 seconds, and left to stand for 3 minutes. Subsequently, centrifugation was performed at 20,400×g for 15 minutes at 4° C., and 500 μL of the supernatant was collected. To the collected supernatant, 500 μL of 70% EtOH was added. The solution was transferred to an RNeasy Mini spin column and centrifuged at 15,000×g for 1 minute at room temperature. The flow through was discarded, and 700 µL of Buffer RW1 (Qiagen) was added to the column, followed by centrifugation at 8,000×g for 1 minute at room temperature. The flow through was discarded, and 500 µL of Buffer RPE (Qiagen) was added to the column, followed by centrifugation at 8,000×g for 1 minute at room temperature. This washing was repeated three times, and finally 50 µL of sterile distilled water was added to the column, followed by centrifugation at 20,400×g for 1 minute at room temperature to extract RNA.

Complementary DNA was synthesized from the extracted RNA using a SMARTer RACE cDNA Amplification Kit (Takara Bio Inc.). Buffer Mix (5×First-Strand buffer 2 µL, 20 mM DTT 1 µL, 10 mM dNTP Mix 1 µL) was adjusted in advance and was left at room temperature. One microliter of 5'-CDS primer-A was taken in a PCR 8-tube strip (Thermo Fisher Scientific, Inc.), 300 ng of total RNA was added thereto, and the total volume was adjusted to 3.75 µL with Nuclease-free Water. The sample was reacted at 72° C. for 3 minutes and then at 42° C. for 2 minutes using a ProFlex PCR system. After spinning down, 1 µL of SMARTerIIA oligo was added thereto. A solution prepared by mixing 4 µL of Buffer Mix, 0.25 µL of RNase inhibitor, and 1 µL of SMART Scribe Reverse Transcriptase was added to the sample. The sample was reacted at 42° C. for 90 minutes and then at 72° C. for 10 minutes using a ProFlex PCR system to synthesize cDNA. The sequence of the cDNA was then analyzed. The sequences of the resulting antibodies were as follows.

The heavy chain variable region of mAb (mouse IgG1) obtained from clone 99 (clone 99-5)

[Formula 6]

```
  1 ATG GAT TGG CTG TGG AAC TTG CTA TTC CTG ATG GCA GCT GCC CAA AGT ATC CAA GCA CAG  60
    M   D   W   L   W   N   L   L   F   L   M   A   A   A   Q   S   I   Q   A   Q

61 ATC CAG TTG GTG CAG TCT GGA CCT GAG CTG AAG AAG CCT GGA GAG ACA GTC AAG ATC TCC 120
    I   Q   L   V   Q   S   G   P   E   L   K   K   P   G   E   T   V   K   I   S
                                                    CDR1
121 TGC AAG GCT TCT GGG TAT ACC TTC ACA AAC TAT GGA ATG AAC TGG GTG AAG CAG GCT CCA 180
    C   K   A   S   G   Y   T   F   T   N   Y   G   M   N   W   V   K   Q   A   P
                                                    CDR2
181 GGA AAG GGT TTA AAG TGG ATG GGC TGG ATA AAC ACC AAA ATT GGA GAG CCA ACA TAT GCT 240
    G   K   G   L   K   W   M   G   W   I   N   T   K   I   G   E   P   T   Y   A

241 GAA GAG TTC AAG GGA CGG TTT GCC TTC TCT TTG GAA ACC TCT GCC AGC ACT GCC TAT TTG 300
    E   E   F   K   G   R   F   A   F   S   L   E   T   S   A   S   T   A   Y   L
                                                                            CDR3
301 CAG ATC AAC AAC CTC AAA AAT GAG GAC ACG GCT ACA TAT TTC TGT GCA AGA CTC CTT GAC 360
    Q   I   N   N   L   K   N   E   D   T   A   T   Y   F   C   A   R   L   L   D

361 TAC TGG GGC CAA GGC ACC ACT CTC ACA GTC TCC TCA GCC AAA ACG ACA CCC CCA TCT GTC 420
    Y   W   G   Q   G   T   T   L   T   V   S   S   A   K   T   T   P   P   S   V
```

The light chain variable region of mAb (mouse IgG1) obtained from clone 99 (clone 99-5)

[Formula 7]

```
  1 ATG GAG ACA GAC ACA CTC CTG CTA TGG GTG CTG CTG CTC TGG GTT CCA GGT TCC ACA GGT  60
    M   E   T   D   T   L   L   L   W   V   L   L   L   W   V   P   G   S   T   G

61 GAC ATT GTG CTG ACC CAA TCT CCA GCT TCT TTG GCT GTG TCT CTA GGG CAG AGG GCC ACC 120
    D   I   V   L   T   Q   S   P   A   S   L   A   V   S   L   G   Q   R   A   T
                        CDR1
121 ATA TCC TGC AGA GCC AGT GAA AGT GTT GAT AGT TAT GGC AAT AGT TTT ATG CAC TGG TAC 180
    I   S   C   R   A   S   E   S   V   D   S   Y   G   N   S   F   M   H   W   Y
                                                                CDR2
181 CAG CAG AAA CCA GGA CAG CCA CCC AAA CTC CTC ATC TAT CGT GCA TCC AAC CTA GAA TCT 240
    Q   Q   K   P   G   Q   P   P   K   L   L   I   Y   R   A   S   N   L   E   S

241 GGG ATC CCT GCC AGG TTC AGT GGC AGT GGG TCT AGG ACA GAC TTC ACC CTC ACC ATT AAT 300
    G   I   P   A   R   F   S   G   S   G   S   R   T   D   F   T   L   T   I   N
                                                        CDR3
301 CCT GTG GAG GCT GAT GAT GTT GCA ACC TAT TAC TGT CAG CAA AGT AAT GAG GAT CCT CGG 360
    P   V   E   A   D   D   V   A   T   Y   Y   C   Q   Q   S   N   E   D   P   R

361 ACG TTC GGT GGA GGC ACC AAG CTG GAA ATC AAA CGG GCT GAT GCT GCA CCA ACT GTA TCC 420
    T   F   G   G   G   T   K   L   E   I   K   R   A   D   A   A   P   T   V   S
```

The heavy chain variable region of mAb (mouse IgG1) obtained from clone 1101

[Formula 8]

```
  1 ATG GAA TGT AAC TGG ATA CTT CCT TTT ATT CTG TCG GTA ATT TCA GGG GTC TAC TCA GAG   60
    M   E   C   N   W   I   L   P   P   I   L   S   V   I   S   G   V   Y   S   E

61 GTT CAG CTC CAG CAG TCT GGG ACT GTG CTG GCA AGG CCT GGG GCT TCC GTG AAA ATG TCC  120
    V   Q   L   Q   Q   S   G   T   V   L   A   R   P   G   A   S   V   K   M   S
                                                      CDR1
121 TGC AAG GCT TCT GGC TTC AGC TTT ACC AGC TAC TGG ATG CAC TGG GTA AAA CAG AGG CCT  180
    C   K   A   S   G   F   S   F   T   S   Y   W   M   H   W   V   K   Q   R   P
                                             CDR2
181 GGA CAG GGT CTA GAA TGG ATT GGT GCT ATT TAT CCT GGA AAT AGT GAT ACT AGA AAC AAC  240
    G   Q   G   L   E   W   I   G   A   I   Y   P   G   N   S   D   T   R   N   N

241 CAG AAG TTC AAG GGC AAG GCC AAA CTG ACT GCA GTC ACA TCC GCC AAC ACT GCC TAC ATG  300
    Q   K   F   K   G   K   A   K   L   T   A   V   T   S   A   N   T   A   Y   M
                                                                              CDR3
301 GAG CTC AGC AGC CTG ACA AAT GAG GAC TCT GCG GTC TAT TAT TGT ACA AGA AAG GCC CAC  360
    E   L   S   S   L   T   N   E   D   S   A   V   Y   Y   C   T   R   K   A   H

361 TAT GGT AAC TAC GGG TTT GCT TAC TGG GGC CAA GGG ACT CTG GTC ACT GTC TCT GCA GCC  420
    Y   G   N   Y   G   F   A   Y   W   G   Q   G   T   L   V   T   V   S   A   A
```

The light chain variable region of mAb (mouse IgG1) obtained from clone 1101

[Formula 9]

```
  1 ATG TCA GGT CAC AGC AGA AAC ATG AAG TTT CCT TCT CAA CTT CTG CTC TTC CTG CTG TTC   60
    M   S   G   H   S   R   N   M   K   F   P   S   Q   L   L   L   F   L   L   F

61 AGA ATC ACA GGC ATA ATA TGT GAC ATC CAG ATG ACA CAA TCT TCA TCC TAC TTG TCT GTA  120
    R   I   T   G   I   I   C   D   I   Q   M   T   Q   S   S   S   Y   L   S   V
                                                      CDR1
121 TCT CTA GGA GGC AGA GTC ACC ATT ACT TGC AAG GCA AGT GAC CAC ATT AAT AAT TGG TTA  180
    S   L   G   G   R   V   T   I   T   C   K   A   S   D   H   I   N   N   W   L
                                                                              CDR2
181 GCC TGG TAT CAG CAG AAA CCA GGA AAT GCT CCT AGG CTC TTA ATA TCT GGT GCA ACC AGT  240
    A   W   Y   Q   Q   K   P   G   N   A   P   R   L   L   I   S   G   A   T   S

241 TTG GAA ACT GGG GTT CCT TCA AGA TTC AGT GGC AGT GGA TCT GGA AAG GAT TAC ACT CTC  300
    L   E   T   G   V   P   S   R   P   S   G   S   G   S   G   K   D   Y   T   L
                                                                      CDR3
301 AGC ATT ACC AGT CTT CAG ACT GAA GAT GTT GCT ACT TAT TAC TGT CAA CAG TAT TGG AGT  360
    S   I   T   S   L   Q   T   E   D   V   A   T   Y   Y   C   Q   Q   Y   W   S

361 ACT CCG CTC ACG TTC GGT GCT GGG ACC AAG CTG GAG CTG AAA CGG GCT GAT GCT GCA CCA  420
    T   P   L   T   F   G   A   G   T   K   L   E   L   K   R   A   D   A   A   P
```

The heavy chain variable region of mAb (mouse IgG2b) obtained from clone 0211

[Formula 10]

```
  1 ATG AAC TTC GGG TTC AGC TTG ATT TTC CTT GTC CTT GTT TTA AAA GGT GTC CAG TGT GAA   60
    M   N   F   G   F   S   L   I   F   L   V   L   V   L   K   G   V   Q   C   E

61 GTG AAG CTG GTG GAG TCT GGG GGA GGC TTA GTG AAG CCT GGA GGG TCC CTG AAA CTC TCC  120
    V   K   L   V   E   S   G   G   G   L   V   K   P   G   G   S   L   K   L   S
                                                      CDR1
121 TGT GCA GCC TCT GGA TTC ACT TTC AGT AGC TAT GCC ATG TCT TGG GTT CGC CAG ACT CCA  180
    C   A   A   S   G   F   T   F   S   S   Y   A   M   S   W   V   R   Q   T   P
                                             CDR2
181 GAG AAG AGG CTG GAG TGG GTC GCA GCC ATT AGT AGT GGT GGT ACC ACC TAC TAT CCA GAC  240
    E   K   R   L   E   W   V   A   A   I   S   S   G   G   T   T   Y   Y   P   D

241 AGT GTG AAG GGC CGA TTC ACC ATC TCC AGA GAT AAT GCC AGG AAC ATC CTG TAC CTG CAA  300
    S   V   K   G   R   F   T   I   S   R   D   N   A   R   N   I   L   Y   L   Q
                                                                              CDR3
301 ATG AGC AGT CTG AGG TCT GAG GAC ACG GCC ATG TAT TAC TGT GTA AGA GGC GGT ACG ATA  360
    M   S   S   L   R   S   E   D   T   A   M   Y   Y   C   V   R   G   G   T   I

361 GGG GCT TAC TGG GGC CAA GGG ACT CTG GTC ACT GTC TCT GCA                          402
    G   A   Y   W   G   Q   G   T   L   V   T   V   S   A
```

The light chain variable region of mAb (mouse IgG2b) obtained from clone 0211

[Formula 11]

```
  1 ATG GAA TCA CAG ACT CAG GTC TTC CTC TCC CTG CTG CTC TGG GTA TCT GGT ACC TGT GGG  60
    M   E   S   Q   T   Q   V   F   L   S   L   L   L   W   V   S   G   T   C   G

61 AAC ATT ATG ATG ACA CAG TCG CCA TCA TCT CTG GCT GTG TCT GCA GGA GAA AAG GTC ACT 120
    N   I   M   M   T   Q   S   P   S   S   L   A   V   S   A   G   E   K   V   T
                        CDR1
121 ATG AGC TGT|AAG TCC AGT CAA AGT GTT TTA TAC AGT TCA AAT CAG AAG AAC TAC TTG GCC|180
    M   S   C  |K   S   S   Q   S   V   L   Y   S   S   N   Q   K   N   Y   L   A |
                                                                         CDR2
181 TGG TAC CAG CAG AAA CCA GGG CAG TCT CCT AAA CTG CTG ATC TAC|TGG GCA TCC ACT AGG|240
    W   V   Q   Q   K   P   G   Q   S   P   K   L   L   I   Y |W   A   S   T   R |

241 |GAA TCT|GGT GTC CCT GAT CGC TTC ACA GGC AGT GGA TCT GGG ACA GAT TTT ACT CTT ACC 300
    |E   S |G   V   P   D   R   F   T   G   S   G   S   G   T   D   F   T   L   T
                                                                CDR3
301 ATC AGC AGT GTA CAA GCT GAA GAC CTG GCA GTT TAT TAC TGT|CAT CAA TAC CTC TCC TCG|360
    I   S   S   V   Q   A   E   D   L   A   V   Y   Y   C  |H   Q   Y   L   S   S |

361 |TGG ACG|TTC GGT GGA GGC ACC AAG CTG GAA ATC AAA                                 396
    |W   T |P   G   G   G   T   K   L   E   I   K
```

SEQUENCE LISTING

SEQ ID NOs: 1 to 3: corresponding to the heavy chain CDR1 to CDR3, respectively, of antibody 99

SEQ ID NO: 4: corresponding to the heavy chain variable region of antibody 99 (amino acid positions 1 to 19 are the signal sequence)

SEQ ID NOs: 5 to 7: corresponding to the light chain CDR1 to CDR3, respectively, of antibody 99

SEQ ID NO: 8: corresponding to the light chain variable region of antibody 99 (amino acid positions 1 to 19 are the signal sequence)

SEQ ID NOs: 9 to 11: corresponding to the heavy chain CDR1 to CDR3, respectively, of antibody 1101

SEQ ID NO: 12: corresponding to the heavy chain variable region of antibody 1101 (amino acid positions. 1 to 19 are the signal sequence)

SEQ ID NOs: 13 to 15: corresponding to the light chain CDR1 to CDR3, respectively, of antibody 1101

SEQ ID NO: 16: corresponding to the light chain variable region of antibody 1101 (amino acid positions 1 to 27 are the signal sequence)

SEQ ID NOs: 17 to 19: corresponding to the heavy chain CDR1 to CDR3, respectively, of antibody 0211

SEQ ID NO: 20: corresponding to the heavy chain variable region of antibody 0211 (amino acid positions 1 to 19 are the signal sequence)

SEQ ID NOs: 21 to 23: corresponding to the light chain CDR1 to CDR3, respectively, of antibody 0211

SEQ ID NO: 24: corresponding to the light chain variable region of antibody 0211 (amino acid positions 1 to 20 are the signal sequence)

SEQ ID NO: 25: human fibrin Bβ chain

SEQ ID NO: 26: human fibrin Bβ chain fragment used as the immunogen of 99

SEQ ID NO: 27: human fibrin Bβ chain fragment used as the immunogen of 1101

SEQ ID NO: 28: human fibrin Bβ chain fragment (No. 2 peptide) that can be used as an immunogen

---

The invention claimed is:

1. An antibody-drug conjugate (ADC), wherein
the antibody is an antibody that binds to fibrin and has affinity to insoluble fibrin higher than that to fibrinogen, the drug is a cytotoxic agent, and
the antibody and the drug are linked to each other through a linker having a plasmin cleavage site that allows cleavage by plasmin, wherein the antibody has
(i) a heavy chain variable region having CDR1 set forth in SEQ ID NO: 1, CDR2 set forth in SEQ ID NO: 2, and CDR3 set forth in SEQ ID NO: 3, and a light chain variable region having CDR1 set forth in SEQ ID NO: 5, CDR2 set forth in SEQ ID NO: 6, and CDR3 set forth in SEQ ID NO: 7;
(ii) a heavy chain variable region having CDR1 set forth in SEQ ID NO: 9, CDR2 set forth in SEQ ID NO: 10, and CDR3 set forth in SEQ ID NO: 11, and a light chain variable region having CDR1 set forth in SEQ ID NO: 13, CDR2 set forth in SEQ ID NO: 14, and CDR3 set forth in SEQ ID NO: 15; or
(iii) a heavy chain variable region having CDR1 set forth in SEQ ID NO: 17, CDR2 set forth in SEQ ID NO: 18, and CDR3 set forth in SEQ ID NO: 19, and a light chain variable region having CDR1 set forth in SEQ ID NO: 21, CDR2 set forth in SEQ ID NO: 22, and CDR3 set forth in SEQ ID NO: 23.

2. The ADC according to claim 1, wherein the linker has a valine-leucine-lysine peptide sequence as the plasmin cleavage site.

3. A pharmaceutical composition comprising the ADC according to claim 1 and a pharmaceutically acceptable excipient.

4. An antibody that binds to fibrin, wherein the antibody has
a heavy chain variable region having CDR1 set forth in SEQ ID NO: 1, CDR2 set forth in SEQ ID NO: 2, and CDR3 set forth in SEQ ID NO: 3, and
a light chain variable region having CDR1 set forth in SEQ ID NO: 5, CDR2 set forth in SEQ ID NO: 6, and CDR3 set forth in SEQ ID NO: 7.

5. The antibody according to claim 4, wherein the antibody has
a heavy chain variable region set forth in SEQ ID NO: 4 and a light chain variable region set forth in SEQ ID NO: 8; or
an antigen-binding fragment thereof.

6. An antibody that binds to fibrin, wherein the antibody has
a heavy chain variable region having CDR1 set forth in SEQ ID NO: 9, CDR2 set forth in SEQ ID NO: 10, and CDR3 set forth in SEQ ID NO: 11, and
a light chain variable region having CDR1 set forth in SEQ ID NO: 13, CDR2 set forth in SEQ ID NO: 14, and CDR3 set forth in SEQ ID NO: 15.

7. The antibody according to claim 6, wherein the antibody has
a heavy chain variable region set forth in SEQ ID NO: 12 and a light chain variable region set forth in SEQ ID NO: 16; or
an antigen-binding fragment thereof.

8. The ADC according to claim 1, wherein the antibody has
a heavy chain variable region having CDR1 set forth in SEQ ID NO: 1, CDR2 set forth in SEQ ID NO: 2, and CDR3 set forth in SEQ ID NO: 3, and
a light chain variable region having CDR1 set forth in SEQ ID NO: 5, CDR2 set forth in SEQ ID NO: 6, and CDR3 set forth in SEQ ID NO: 7
or an antigen-binding fragment thereof.

9. A pharmaceutical composition comprising the ADC according to claim 8 and a pharmaceutically acceptable excipient.

10. The ADC according to claim 1, wherein the antibody has
a heavy chain variable region having CDR1 set forth in SEQ ID NO: 9, CDR2 set forth in SEQ ID NO: 10, and CDR3 set forth in SEQ ID NO: 11, and
a light chain variable region having CDR1 set forth in SEQ ID NO: 13, CDR2 set forth in SEQ ID NO: 14, and CDR3 set forth in SEQ ID NO: 15.

11. A pharmaceutical composition comprising the ADC according to claim 10 and a pharmaceutically acceptable excipient.

* * * * *